(12) United States Patent
Valys et al.

(10) Patent No.: US 11,877,830 B2
(45) Date of Patent: Jan. 23, 2024

(54) MACHINE LEARNING HEALTH ANALYSIS WITH A MOBILE DEVICE

(71) Applicant: AliveCor, Inc., Mountain View, CA (US)

(72) Inventors: Alexander Vainius Valys, Sunnyvale, CA (US); Frank Losasso Petterson, Los Altos Hills, CA (US); Conner Daniel Cross Galloway, Sunnyvale, CA (US); David E. Albert, Oklahoma City, OK (US); Ravi Gopalakrishnan, San Francisco, CA (US); Lev Korzinov, San Francisco, CA (US); Fei Wang, San Francisco, CA (US); Euan Thomson, Los Gatos, CA (US); Nupur Srivastava, San Francisco, CA (US); Omar Dawood, San Francisco, CA (US); Iman Abuzeid, San Francisco, CA (US)

(73) Assignee: ALIVECOR, INC., Mountain View, CA (US)

( * ) Notice: Subject to any disclaimer, the term of this patent is extended or adjusted under 35 U.S.C. 154(b) by 256 days.

(21) Appl. No.: 16/580,574

(22) Filed: Sep. 24, 2019

(65) Prior Publication Data

US 2020/0107733 A1 Apr. 9, 2020
US 2020/0281485 A9 Sep. 10, 2020

Related U.S. Application Data

(63) Continuation of application No. 16/153,403, filed on Oct. 5, 2018, now abandoned.
(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0022* (2013.01); *A61B 5/0245* (2013.01);
(Continued)

(58) Field of Classification Search
CPC ..... A61B 5/02055; A61B 5/361; A61B 5/349; A61B 5/0022; A61B 5/02405;
(Continued)

(56) References Cited

U.S. PATENT DOCUMENTS

2009/0240113 A1* 9/2009 Heckerman ............ A61B 5/681
600/300
2010/0249629 A1* 9/2010 Schmidt .................. A61B 7/04
600/528

(Continued)

FOREIGN PATENT DOCUMENTS

WO 2017117798 A1 7/2017

OTHER PUBLICATIONS

Serkan Kiranyaz et al., "Real-Time Patient—Specific ECG Classification by 1-D Convolutional Neural networks", IEEE Transactions on Biomedical Engineering., vol. 63, No. 3, Mar. 1, 2016, pp. 664-675.
(Continued)

*Primary Examiner* — Lynsey C Eiseman
*Assistant Examiner* — Jessandra F Hough
(74) *Attorney, Agent, or Firm* — Womble Bond Dickinson (US) LLP

(57) ABSTRACT

Disclosed herein are devices, systems, methods and platforms for continuously monitoring the health status of a user, for example the cardiac health status. The present disclosure describes systems, methods, devices, software, and platforms for continuously monitoring a user's low-fidelity health-indicator data (for example and without limitation PPG signals, heart rate or blood pressure) from a user-device
(Continued)

in combination with corresponding (in time) data related to factors that may impact the health-indicator ("other-factors") to determine whether a user has normal health as judged by or compared to, for example and not by way of limitation, either (i) a group of individuals impacted by similar other-factors, or (ii) the user him/herself impacted by similar other-factors.

20 Claims, 14 Drawing Sheets

Related U.S. Application Data

(60) Provisional application No. 62/589,477, filed on Nov. 21, 2017, provisional application No. 62/569,309, filed on Oct. 6, 2017.

(51) Int. Cl.

| | | |
|---|---|---|
| *A61B 5/024* | (2006.01) | |
| *A61B 5/0245* | (2006.01) | |
| *G16H 50/20* | (2018.01) | |
| *G16Z 99/00* | (2019.01) | |
| *G16H 40/63* | (2018.01) | |
| *G16H 40/67* | (2018.01) | |
| *G16H 50/70* | (2018.01) | |
| *A61B 5/349* | (2021.01) | |
| *A61B 5/361* | (2021.01) | |
| *G16H 50/30* | (2018.01) | |
| *A61B 5/11* | (2006.01) | |
| *A61B 5/021* | (2006.01) | |
| *G16H 10/60* | (2018.01) | |
| *G16H 15/00* | (2018.01) | |

(52) U.S. Cl.
CPC ...... *A61B 5/02405* (2013.01); *A61B 5/02416* (2013.01); *A61B 5/349* (2021.01); *A61B 5/361* (2021.01); *A61B 5/681* (2013.01); *A61B 5/7264* (2013.01); *A61B 5/7267* (2013.01); *A61B 5/7275* (2013.01); *A61B 5/742* (2013.01); *A61B 5/746* (2013.01); *G16H 40/63* (2018.01); *G16H 40/67* (2018.01); *G16H 50/20* (2018.01); *G16H 50/70* (2018.01); *G16Z 99/00* (2019.02); *A61B 5/021* (2013.01); *A61B 5/02438* (2013.01); *A61B 5/1118* (2013.01); *A61B 5/6898* (2013.01); *G16H 10/60* (2018.01); *G16H 15/00* (2018.01); *G16H 50/30* (2018.01)

(58) Field of Classification Search
CPC ... A61B 5/02416; A61B 5/0245; A61B 5/681; A61B 5/7264; A61B 5/7267; A61B 5/7275; A61B 5/742; A61B 5/746; A61B 5/021; A61B 5/02438; A61B 5/1118; A61B 5/6898; G16H 40/67; G16H 40/63; G16H 50/70; G16H 50/20; G16H 50/30; G16H 10/60; G16H 15/00; G16Z 99/00; G06F 19/00

See application file for complete search history.

(56) References Cited

U.S. PATENT DOCUMENTS

| | | | |
|---|---|---|---|
| 2011/0066043 A1* | 3/2011 | Banet | A61B 5/022 |
| | | | 600/485 |
| 2013/0289364 A1* | 10/2013 | Colman | A61B 10/00 |
| | | | 600/301 |
| 2015/0164349 A1* | 6/2015 | Gopalakrishnan ... | A61B 5/0022 |
| | | | 600/508 |
| 2015/0193595 A1* | 7/2015 | McNamara | A61B 5/0022 |
| | | | 705/2 |
| 2016/0331247 A1 | 11/2016 | Albert | |
| 2017/0135585 A1 | 5/2017 | Liu et al. | |
| 2017/0290550 A1 | 10/2017 | Perschbacher et al. | |

OTHER PUBLICATIONS

International Search Report for the International application No. PCT/US2019/054882, dated Nov. 25, 2019.

International Search Report and Written Opinion dated Jan. 23, 2019 for International Application No. PCT/US2018/054714 in 13 pages.

Lau et al. "iPhone ECG application for community screening to detect silent atrial fibrillation: A novel technology to prevent stroke", International Journal of Cardiology, vol. 165, No. 1, Mar. 7, 2013, pp. 193-194.

* cited by examiner

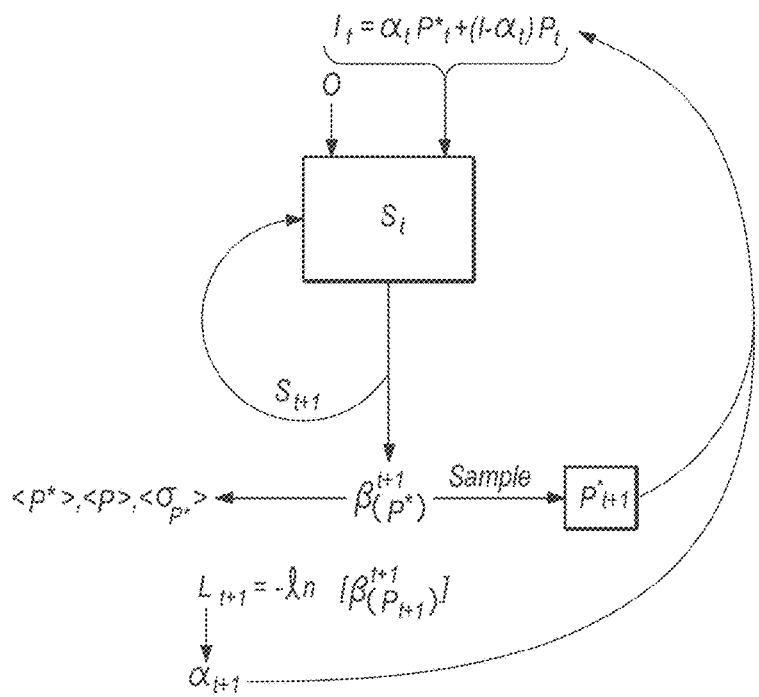
FIG. 5C
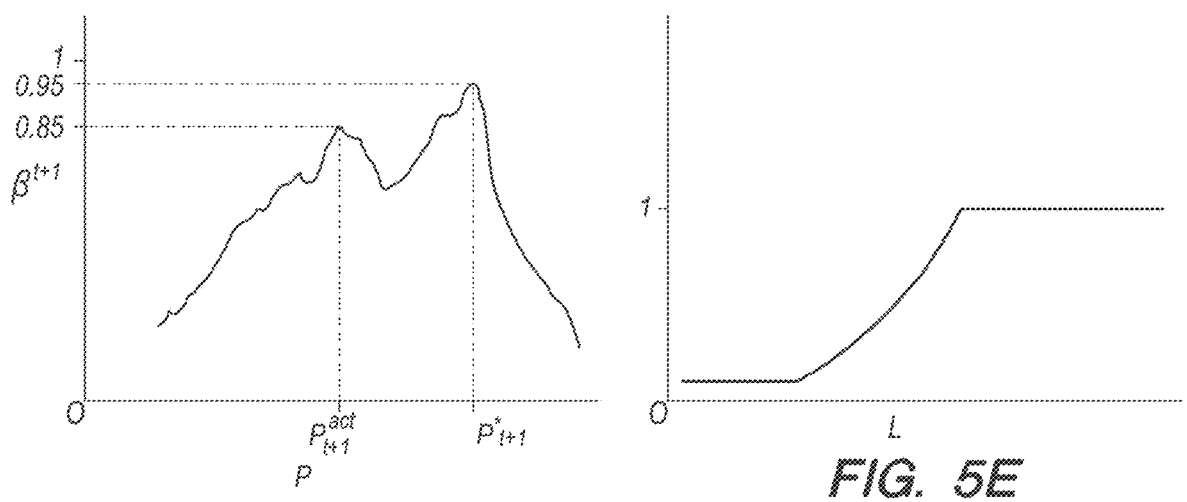
FIG. 5D
FIG. 5E

MACHINE LEARNING HEALTH ANALYSIS WITH A MOBILE DEVICE

CROSS-REFERENCE TO RELATED APPLICATIONS

This application is a continuation of U.S. application Ser. No. 16/153,403, filed Oct. 5, 2018, the entire contents of which are hereby incorporated by reference.

BACKGROUND

Indicators of an individual's physiological health ("health-indicators")—for example, and not by way of limitation: heart rate, heart rate variability, blood pressure, and ECG (electrocardiogram) to name a few—can be measured or calculated at any discrete point or points in time from data collected to measure the health-indicators. In many cases, the value of the health-indicator at a particular time, or a change over time provides information regarding the state of an individual's health. A low or high heart rate or blood pressure, or an ECG that clearly demonstrate myocardial ischemia, for example, may demonstrate the need for immediate intervention. But, readings, a series of readings, or changes to the readings over time of these indicators may provide information not recognized by the user or even a health professional as needing attention.

Arrhythmias, for example, may occur continuously or may occur intermittently. Continuously occurring arrhythmias may be diagnosed most definitively from an electrocardiogram of an individual. Because a continuous arrhythmia is always present, ECG analysis may be applied at any time in order to diagnose the arrhythmia. An ECG may also be used to diagnose intermittent arrhythmias. However, because intermittent arrhythmias may be asymptomatic and/or are by definition intermittent, diagnosis presents challenges of applying the diagnostic technique at the time when the individual is experiencing the arrhythmia. Thus, actual diagnosis of intermittent arrhythmias is notoriously difficult. This particular difficulty is compounded with asymptomatic arrhythmias, which account for nearly 40% of arrhythmias in the US. Boriani G. and Pettorelli D., Atrial Fibrillation Burden and Atrial Fibrillation type: Clinical Significance and Impact on the Risk of Stroke and Decision Making for Long-term Anticoagulation, *Vascul Pharmacol.*, 83:26-35 (August 2016), pp. 26.

Sensors and mobile electronics technologies exist which permit frequent or continuous monitoring and recording of health-indicators. However, the capability of these sensor platforms often exceeds that of conventional medical science to interpret the data they produce. The physiological significance of health-indicator parameters, like heart rate, are frequently well defined only in specific medical contexts: for instance, heart rate is conventionally evaluated as a single scalar value out of context from other data/information that may impact the health-indicator. A resting heart rate in the range of 60-100 beats per minute (BPM) may be considered normal. A user may generally measure their resting heart rate manually once or twice per day.

A mobile sensor platform (for example: a mobile blood pressure cuff; mobile heart rate monitor; or mobile ECG device) may be capable of monitoring the health-indicator (e.g., heart rate) continuously, e.g., producing a measurement every second or every 5 seconds, while simultaneously also acquiring other data about the user such as and without limitation: activity level, body position, and environmental parameters like air temperature, barometric pressure, location, etc. In a 24-hour period, this may result in many thousands of independent health-indicator measurements. In contrast to a measurement once or twice a day, there is relatively little data or medical consensus on what a "normal" sequence of thousands of measurements looks like.

Devices presently used to continuously measure health-indicators of users/patients range from bulky, invasive, and inconvenient to simple wearable or handheld mobile devices. Presently, these devices do not provide the capability to effectively utilize the data to continuously monitor a person's heath. It is up to a user or health professional to assess the health-indicators in light of other factors that may impact these health-indicators to determine the health status of the user.

BRIEF DESCRIPTION OF THE DRAWINGS

Certain features described herein are set forth with particularity in the appended claims. A better understanding of the features and advantages disclosed embodiments will be obtained by reference to the following detailed description that sets forth illustrative embodiments, in which the principles described herein are utilized, and the accompanying drawings of which:

FIGS. 5A-5E depict alternative recurrent neural networks in accordance with some embodiments as described herein and hypothetical plots used to describe some of these embodiments;

DETAILED DESCRIPTION

Figures 1A, 1B:
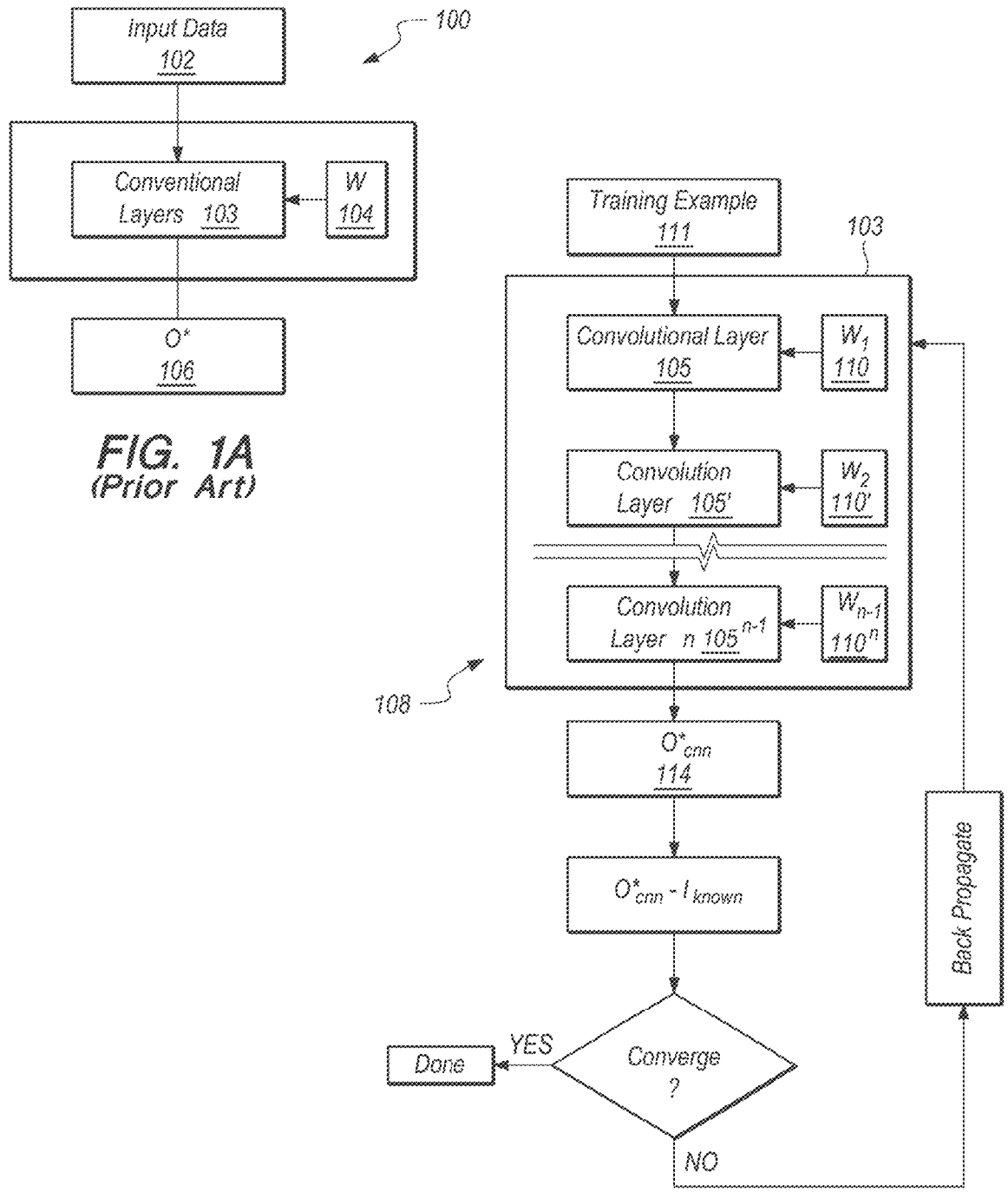
FIGS. 1A-1B depict a convolutional neural network that may be used accordance with some embodiments as described herein.

The high volume of data, complexity of interactions between health-indicators and other-factors and limited clinical guidance may limit the effectiveness of any monitoring system that attempts to detect abnormalities in continuous and/or ambulatory sensor data through specific rules based on conventional medical practice. Embodiments described herein include devices, systems, methods, and platforms that can detect abnormalities in an unsupervised fashion from time sequences of health-indicator data alone or in combination with other-factor (as defined herein) data utilizing predictive machine learning models.

Atrial fibrillation (AF or AFib) is found in 1-2% of the general population, and the presence of AF increases risk of morbidity and adverse outcomes such as stroke and heart failure. Boriani G. and Pettorelli D., Atrial Fibrillation Burden and Atrial Fibrillation type: Clinical Significance and Impact on the Risk of Stroke and Decision Making for Long-term Anticoagulation, *Vascul Pharmacol.*, 83:26-35 (August 2016), pp. 26. AFib in many people, some estimate as high as 40% of AF patients, may be asymptomatic, and these asymptomatic patients have similar risk profiles for stroke and heart failure as symptomatic patients. See, id. However, the symptomatic patients can take active measures, such as taking blood thinners or other medications, to reduce the risks of negative outcomes. Use of implantable electrical devices (CIEDs) can detect asymptomatic AF (so-called silent AF or SAF) and the duration the patient is in AF. Id. From this information, the time these patients spend in AF, or AF-burden can be determined. Id. An AF-burden of greater than 5-6 min and particularly greater than 1 hour is associated with significant increased risk of stroke and other negative health outcomes. Id. Thus, the ability to measure AF-burden in asymptomatic patients can lead to earlier interventional therapies and may reduce risks of negative health outcomes associated with AF. Id. Detection of SAF is challenging, typically requiring some form of continuous monitoring. Presently continuous monitoring for AF requires bulky, sometimes invasive, and expensive devices, where such monitoring requires a high level of medical professional oversight and review.

Many devices continuously obtain data to provide a measurement or calculation of the health-indicator data, for example and without limitation FitBit®, Apple Watch®, Polar®, smart phones, tablets among others are in the class of wearable and/or mobile devices. Other devices include permanent or semi-permanent devices on or in a user/patient (e.g., holter), and others may include larger devices in hospitals that may be mobile by virtue of being on a cart. But, little is done with this measured data other than periodically observing it on a display or establishing simple data-thresholds. Observation of the data, even by trained medical professionals, may frequently appear as normal, one primary exception being when a user has readily identifiable acute symptoms. It is tremendously difficult and practically impossible for medical professionals to continuously monitor health-indicators to observe anomalies and/or trends in data that may be indicative of something more serious.

As used herein, a platform comprises one or more customized software applications (or "applications") configured to interact with one another either locally or through a distributed network including the cloud and the Internet. Applications of a platform as described herein are configured to collect and analyze user data and may include one or more software models. In some embodiments of the platform, the platform includes one or more hardware components (e.g. one or more sensing devices, processing devices, or microprocessors). In some embodiments, a platform is configured to operate together with one or more devices and/or one or more systems. That is, a device as described herein, in some embodiments, is configured to run an application of a platform using a built-in processor, and in some embodiments, a platform is utilized by a system comprising one or more computing devices that interact with or run one or more applications of the platform.

The present disclosure describes systems, methods, devices, software, and platforms for continuously monitoring a user's data related to one or more health-indicators (for example not by way of limitation PPG signals, heart rate or blood pressure) from a user-device in combination with corresponding (in time) data related to factors that may impact the health-indicator (referred to herein as "other-factors") to determine whether a user has normal health as judged by or compared to, for example and not by way of limitation, either (i) a group of individuals impacted by similar other-factors, or (ii) the user him/herself impacted by similar other-factors. In some embodiments, measured health-indicator data alone or in combination with other-factor data is input into a trained machine learning model that determines a probability the user's measured health-indicator is considered within a healthy range, and if not to notify the user of such. The user not being in a healthy range may increase the likelihood the user may be experiencing a health event warranting high-fidelity information to confirm a diagnosis, such as an arrhythmia which may be symptomatic or asymptomatic. The notification may take the form of, for example, requesting the user to obtain an ECG. Other high-fidelity measurements may be requested, blood pressure, pulse oximeter to name two, ECG is but one example. The high-fidelity measurement, ECG in this embodiment, can be evaluated by algorithms and/or medical professionals to make a notification or diagnosis (collectively referred to herein as "diagnosis", recognizing that only a physician can make a diagnosis). In the ECG example, the diagnosis may be AFib or any other number of well-known conditions diagnosed utilizing ECGs.

In further embodiments, a diagnosis is used to label a low-fidelity data sequence (e.g., heart rate or PPG), which may include the other-factor data sequence. This high-fidelity diagnosis-labeled low-fidelity data sequence is used to train a high-fidelity machine learning model. In these further embodiments, the training of the high-fidelity machine learning model may be trained by unsupervised learning or may be updated from time to time with new training examples. In some embodiments, a user's measured low-fidelity health-indicator data sequence and optionally a corresponding (in time) data sequence of other-factors are input into the trained high-fidelity machine learning models to determine a probability and/or prediction the user is experiencing or experienced the diagnosed condition on which the high-fidelity machine learning model was trained. This probability may include a probability of when the event begins and when it ends. Some embodiments, for example, may calculate the atrial fibrillation (AF) burden of a user, or the amount of time a user experiences AF over time. Previously AF burden could only be determined using cumbersome and expensive holter or implantable continuous ECG monitoring apparatus. Thus, some embodiments described herein can continuously monitor a user's health status and notify the user of a health status change by continuously monitoring health-indicator data (for example and not by way of limitation PPG data, blood pressure data, and heart rate data) obtained from a user worn device alone or in combination with corresponding data for other-factors. "Other-factors", as used herein, include anything that may impact the health-indicator, and/or may impact the data representing the health-indicator (e.g., PPG data). These other-factors may include a variety of factors such as by way of example not limitation: air temperature, altitude, exercise levels, weight, gender, diet, standing, sitting, falling, lying down, weather, and BMI to name a few. In some embodiments a mathematical or empirical model not a machine learning model may be used to determine when to notify a user to obtain a high-fidelity measurement, which can then be analyzed and used to train a high-fidelity machine training models as described herein.

Some embodiments described herein can detect abnormalities of a user in an unsupervised fashion by: receiving a primary time sequence of health-indicator data; optionally receiving one or more secondary time sequences of other-factor data, corresponding in time with the primary time sequence of health-indicator data, which secondary sequences may come from a sensor, or from external data sources (e.g. over a network connection, a computer API, etc.); providing the primary and secondary time sequence(s) to a pre-processor, which may perform operations on the data like filtering, caching, averaging, time alignment, buffering, upsampling and downsampling; providing the time sequences of data to a machine learning model, trained and/or configured to utilize the values of the primary and secondary time sequence(s) to predict next value(s) of the primary sequence at a future time; comparing the predicted primary time sequence values(s) generated by the machine learning module at a specific time t to the measured values of the primary time sequence at time t; and alerting or prompting the user to take an action if the difference between the predicted future time sequence and measured time sequences exceeds a threshold or criteria.

Some embodiments described herein, thus, detect when the observed behavior of the primary sequence of physiological data with respect to the passage of time and/or in response to the observed secondary sequence of data differs from what is expected given the training examples used to train the model. When the training example is gathered from normal individuals or from data that has been previously categorized as normal for a specific user, then the system can serve as an abnormality detector. If the data has simply been acquired from a specific user without any other categorization, then the system can serve as a change detector, detecting a change in the health-indicator data that the primary sequence is measuring relative to the time at which the training data was captured.

Described herein are software platforms, systems, devices, and methods for generating and using trained machine learning models to predict or determine a probability when a user's measured health-indicator data (primary sequence) under the influence of other-factor(s) (secondary sequence) is outside the bounds of normal for a healthy population (i.e., a global model) under the influence of similar other-factors, or outside the bounds of normal for that particular user (i.e., personalized model) under the influence of similar other-factors, where a notification of such is provided to the user. In some embodiments, the user may be prompted to obtain additional measured high-fidelity data that can be used to label previously acquired low-fidelity user health-indicator data to generate a different trained high-fidelity machine learning model that has the ability to predict or diagnose abnormalities or events using only low-fidelity health-indicator data, where such abnormalities are typically only identified or diagnosed using high-fidelity data.

Some embodiments described herein may include inputting a user's health-indicator data, and optionally inputting corresponding (in time) data of other-factors into a trained machine learning model, where the trained machine learning model predicts the user's health-indicator data or a probability distribution of the health-indicator data at a future time step. The prediction in some embodiments is compared with the user's measured health-indicator data at the time step of the prediction, where, if the absolute value of the difference exceeds a threshold, the user is notified that his or her health-indicator data is outside a normal range. This notification, in some embodiments, may include a diagnosis or instructions to do something, for example and not by way of limitation obtain additional measurements or contact a health professional. In some embodiments, health-indicator data and corresponding (in time) data of other-factors from a healthy population of people is used to train the machine learning model. It will be appreciated that the other-factors in training examples used to train the machine learning model may not be averages of the population, rather data for each of the other-factors corresponds in time with collection of the health-indicator data for individuals in the training examples.

Some embodiments are described as receiving discrete data points in time, predicting discrete data points at a future time from the input and then determining if a loss between discrete measured input at the future time and the predicted value at the future time exceeds a threshold. The skilled artisan will readily appreciate that the input data and output predictions may take forms other than a discrete data point or a scalar. For example, and not by way of limitation, the health-indicator data sequence (also referred to herein as primary sequence) and the other-data sequence (also referred to herein as secondary sequence) may be split into segments of time. The skilled artisan will recognize the manner in which the data is segmented is a matter of design choice and may take many different forms.

Some embodiments partition the health-indicator data sequence (also referred to herein as primary sequence) and the other-data sequence (also referred to herein as secondary sequence) into two segments: past, representing all data before a specific time t, and future, representing all data at or after time t. These embodiments input the health-indicator data sequence for a past time segment and all other-data sequence(s) for the past time segment into a machine learning model configured to predict the most probable future segment of the health-indicator data (or distribution of probable future segments). Alternatively, these embodiments input the health-indicator data sequence for a past time segment, all other-data sequences for the past time segment and other-data sequences from the future segment into a machine learning model configured to predict the most probable future segment of the health-indicator data (or distribution of probable future segments). The predicted future segment of the health-indicator data is compared to the user's measured health-indicator data at the future segment to determine a loss and whether the loss exceeds a threshold, in which case some action is taken. The action may include for example and not by way of limitation: notifying the user to obtain additional data (e.g., ECG or blood pressure); notifying the user to contact a healthcare professional, or automatically triggering acquisition of additional data. Automatic acquisition of additional data may include, for example and not by way of limitation, ECG acquisition via a sensor operably coupled (wired or wirelessly) to a user worn computing device, or blood pressure via a mobile cuff around the user's wrist or other appropriate body part and coupled to a user worn computing device. The segments of data may include a single data point, many data points over a period of time, an average of these data points over the time period where the average may include a true average, median or mode. In some embodiments the segments may overlap in time.

These embodiments detect when the observed behavior or measurement of the health-indicator sequence of data with respect to the passage of time as impacted by corresponding (in time) other-factor sequence of data differs from what is expected from the training examples, which training examples are collected under similar other-factors. If the training examples are gathered from healthy individuals under similar other-factors or from data that has been previously categorized as healthy for a specific user under similar other-factors, then these embodiments serve as an abnormality detector from the healthy population or from the specific user, respectively. If the training examples have simply been acquired from a specific user without any other categorization, then these embodiments serve as a change detector, detecting a change in the health-indicators at the time of measurement relative to the time at which the training examples were collected for the specific user.

Some embodiments described herein utilize machine learning to continuously monitor a person's health-indicators under the impact of one or more other-factors and assess whether the person is healthy in view a population categorized as healthy under the impact of similar other factors. As the skilled artisan will readily appreciate, a number of different machine learning algorithms or models (including without limitation Bayes, Markov, Gaussian processes, clustering algorithms, generative models, kernel and neural network algorithms) may be used without exceeding the scope described herein. As appreciated by the skilled artisan, typical neural networks employ, by way of example not limitation, one or more layers of nonlinear activation functions to predict an output for a received input, and may include one or more hidden layers in addition to the input and output layers. The output of each hidden layer in some of these networks is used as input to the next layer in the network. Examples of neural networks include, by way of example and not limitation, generative neural networks, convolutional neural networks and recurrent neural networks.

Some embodiments of a health monitoring system monitor heart rate and activity data of an individual as low-fidelity data (e.g., heartrate or PPG data) and detect a condition (e.g. AFib) normally detected using high-fidelity data (e.g., ECG data). For example, the heart rate of an individual may be provided by a sensor continuously or in discrete intervals (such as every five seconds). The heart rate may be determined based on PPG, pulse oximetry, or other sensors. In some embodiments, the activity data may be generated as a number of steps taken, an amount of movement sensed, or other data points indicating an activity level. The low-fidelity (e.g., heartrate) data and activity data can then be input into a machine learning system to determine a prediction of a high-fidelity outcome. For example, the machine learning system may use the low-fidelity data to predict an arrhythmia or other indication of a user's cardiac health. In some embodiments, the machine learning system may use an input of segment of data inputs to determine a prediction. For example, an hour of activity level data and heart rate data may be input to the machine learning system. The system can then use the data to generate a prediction of a condition such as atrial fibrillation. Various embodiments of the present invention are more thoroughly discussed below.

Referring to FIG. 1A a trained convolution neural network (CNN) 100 (one example of a feed forward network), takes input data 102, (e.g., a picture of a boat) into convolutional layers (aka hidden layers) 103, applies a series of trained weights or filters 104 to the input data 106 in each of the convolutional layers 103. The output of the first convolutional layer is an activation map (not shown), which is the input to the second convolution layer, to which a trained weight or filter (not shown) is applied, where the output of the subsequent convolutional layers results in activation maps that represent more and more complex features of the input data to the first layer. After each convolutional layer a non-linear layer (not shown) is applied to introduce non-linearity into the problem, which nonlinear layers may include tan h, sigmoid or ReLU. In some cases, a pooling layer (not shown) may be applied after the nonlinear layers, also referred to as a downsampling layer, which basically takes a filter and stride of the same length and applies it to the input, and outputs the maximum number in every sub-region the filter convolves around. Other options for pooling are average pooling and L2-norm pooling. The pooling layer reduces the spatial dimension of the input volume reducing computational costs and to control over-fitting. The final layer(s) of the network is a fully connected layer, which takes the output of the last convolutional layer and outputs an n-dimensional output vector representing the quantity to be predicted, e.g., probabilities of image classification 20%/o automobile, 75% boat 5% bus and 0% bicycle, i.e., resulting in predictive output 106 (O*), e.g. this is likely a picture of a boat. The output could be a scalar value data point being predicted by the network, a stock price for example. Trained weights 104 may be different for each of the convolutional layers 103, as will be described more fully below. To achieve this real-world prediction/detection (e.g., it's a boat), the neural network needs to be trained on known data inputs or training examples resulting in trained CNN 100. To train CNN 100 many different training examples (e.g., many pictures of boats) are input into the model. A skilled artisan in neural networks will fully understand the description above provides a somewhat simplistic view of CNNs to provide some context for the present discussion and will fully appreciate the application of any CNN alone or in combination with other neural networks will be equally applicable and within the scope of some embodiments described herein.

FIG. 1B demonstrates training CNN 108. In FIG. 1B convolutional layers 103 are shown as individual hidden convolutional layers 105, 105' up to convolutional layer $105^{n-1}$ and the final $n^{th}$ layer is a fully connected layer. It will be appreciated that last layers may be more than one fully connected layer. Training example 111 is input into convolutional layers 103, a nonlinear activation function (not shown) and weights 110, 110' through $110''$ are applied to training example 111 in series, where the output of any hidden layer is input to the next layer, and so on until the final $n^{th}$ fully connected layer $105^n$ produces output 114. Output or prediction 114 is compared against training example 111 (e.g., picture of a boat) resulting in difference 116 between output or prediction 114 and training example 111. If difference or loss 116 is less than some preset loss (e.g., output or prediction 114 predicts the object is a boat), the CNN is converged and considered trained. If the CNN has not converged, using the technique of backpropagation, weights 110 and 110' through $110''$ are updated in accordance with how close the prediction is to the known input. The skilled artisan will appreciate that methods other than back propagation may be used to adjust the weights. The second training example (e.g., different picture of a boat) is input and the process repeated again with the updated weights, which are then updated again and so on until the $n^{th}$ training example (e.g., $n^{th}$ picture of $n^{th}$ boat) has been input. This is repeated over and over with the same n-training examples until the convolutional neural network (CNN) is trained or converges on the correct outputs for the known inputs. Once CNN 108 is trained, weights 110, 110' through $110''$ are fixed and used in trained CNN 100, which are weights 104 as depicted in FIG. 1A. As explained, there are different weights for each convolutional layer 103 and for each of the fully connected layers. The trained CNN 100 or model is then fed image data to determine or predict that which it is trained to predict/identify (e.g., a boat), as described above. Any trained model, CNN, RNN, etc. may be trained further, i.e., modification of the weights may be permitted, with additional training examples or with predicted data output by the model which is then used as a training example. The machine learning model can be trained "offline", e.g. trained once on a computational platform separate from the platform using/executing the trained model, and then transferred to that platform. Alternatively, embodiments described herein may periodically or continually update the machine learning model based on newly acquired training data. This updated training may occur on a separate computational platform which delivers the updated trained models to the platform using/executing the re-trained model over a network connection, or the training/re-training/update process may occur on the platform itself as new data is acquired. The skilled artisan will appreciate the CNN is applicable to data in a fixed array (e.g., a picture, character, word etc.) or a time sequence of data. For example, sequenced health-indicator data and other-factor data can be modeled using a CNN. Some embodiments utilize a feed-forward, CNN with skip connections and a Gaussian Mixture Model output to determine a probability distribution for the predicted health-indicator, e.g., heart rate, PPG, or arrhythmia.

Some embodiments can utilize other types and configurations of neural network. The number of convolutional layers can be increased or decreased, as well as the number of fully-connected layers. In general, the optimal number and proportions of convolutional vs. fully-connected layers can be set experimentally, by determining which configuration gives the best performance on a given dataset. The number of convolutional layers could be decreased to 0, leaving a fully-connected network. The number of convolutional filters and width of each filter can also be increased or decreased.

The output of the neural network may be a single, scalar value, corresponding to an exact prediction for the primary time sequence. Alternatively, the output of the neural network could be a logistic regression, in which each category corresponds to a specific range or class of primary time sequence values, are any number of alternative outputs readily appreciated by the skilled artisan.

The use of a Gaussian Mixture Model output in some embodiments is intended to constrain the network to learning well-formed probability distributions and improve generalization on limited training data. The use of a multiple elements in some embodiments in the Gaussian Mixture Model is intended to allow the model to learn multi-modal probability distributions. A machine learning model combining or aggregating the results of different neural networks could also be used, where the results could be combined.

Figures 2A, 2B:
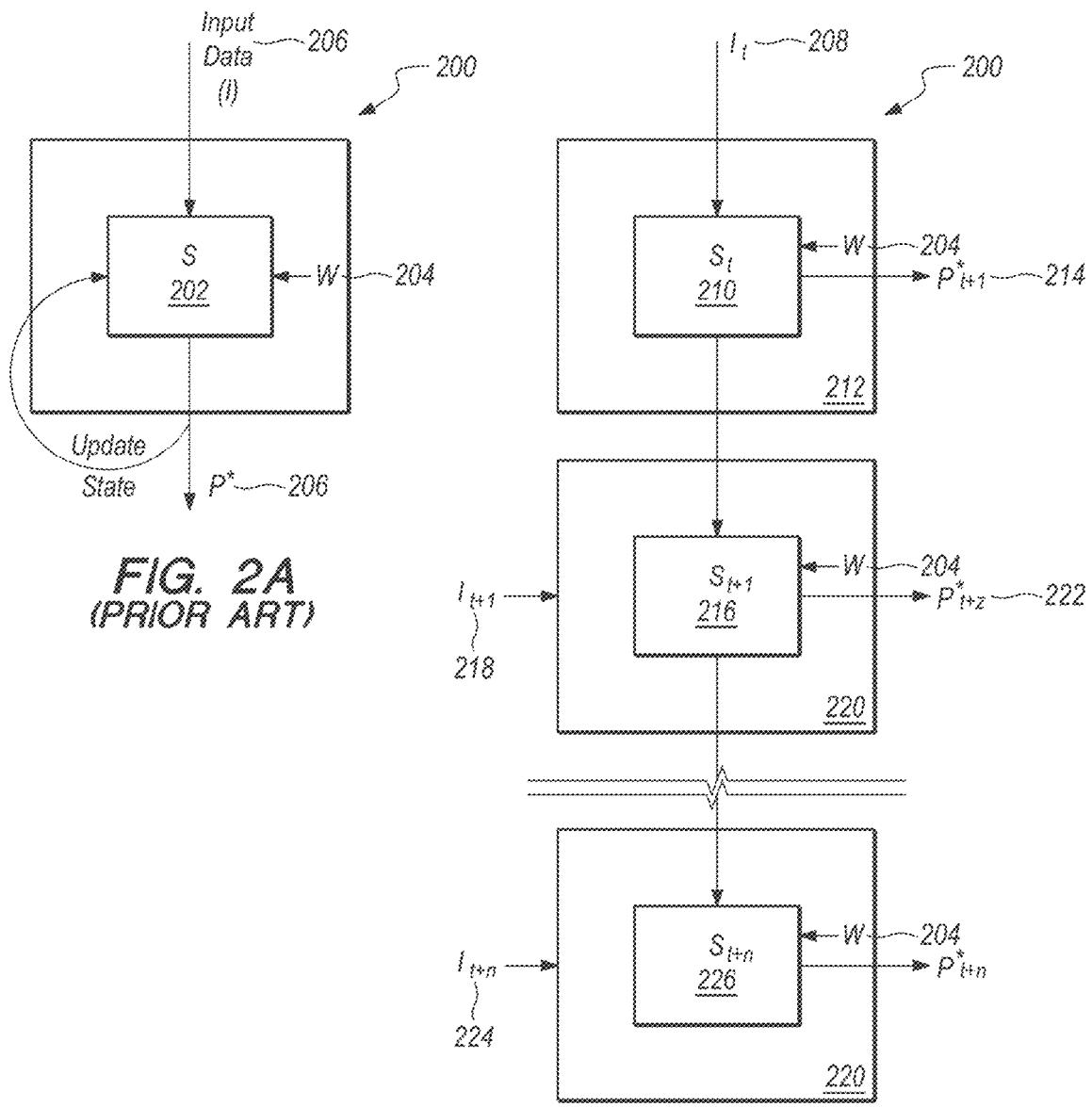
FIGS. 2A-2B depict a recurrent neural network that may be used in accordance with some embodiments as described herein.

Machine learning models that have an updatable memory or state from previous predictions to apply to subsequent predictions is another approach for modeling sequenced data. In particular, some embodiments described herein utilize a recurring neural network. Referring to the example of FIG. 2A a diagram of a trained recurrent neural network (RNN) 200 is shown. Trained RNN 200 has updatable state (S) 202 and trained weights (W) 204. Input data 206 is input into sate 202 where weights (W) 204 are applied, and prediction 206 (P*) is output. In contrast to linear neural networks (e.g., CNN 100), state 202 is updated based on the input data, thereby serving as memory from the previous state for the next prediction with the next data in sequence. Updating the sates gives RNNs a circular or loop feature. To better demonstrate, FIG. 2B shows trained RNN 200 unrolled, and its applicability to sequenced data. Unrolled, the RNN appears analogous to a CNN, but in an unrolled RNN each of the apparently analogous layers appears as a single layer with an updated state, where the same weights are applied in each iteration of the loop. The skilled artisan will appreciate the single layer may itself have sub-layers, though for clarity of explanation a single layer is depicted here. Input data ($I_t$) 208 at time t is input into state-at-time t ($S_t$) 210 and trained weights 204 are applied within cell-at-time t ($C_t$) 212. The output of $C_t$ 212 is prediction-at time step t+1 ($P^*_{t+1}$) 214 and updated state $S_{t+1}$ 216. Similarly, in $C_{t+1}$ 220 $I_{t+1}$ 218 is input into $S_{t+1}$ 216, the same trained weights 204 are applied, and the output of $C_{t+1}$ 220 is $P^*_{t+2}$ 222. As noted above $S_{t+1}$ is updated from $S_t$, therefor $S_{t+1}$ has memory from $S_t$ from the previous time step. For example, and not by way of limitation, this memory may include previous health-indicator data or previous other-factor data from one or more previous time steps. This process continues for n-steps, where $I_{t+n}$ 224 is input into $S_{t+n}$ 226 and the same weights 204 are applied. The output of cell $C_{t+n}$ is prediction $P^*_{t+n}$. Notably, the states are updated from previous time steps giving RNNs the benefit of memory from a previous state. This characteristic makes RNNs an alternative choice to make predictions on sequenced data for some embodiments. Though, and as described above, there are other suitable machine learning techniques for performing such predictions on sequenced data, including CNNs.

RNNs, like CNNs, can handle a string of data as input, and output a predicted string of data. A simple way to explain this aspect of using an RNN is using the example of natural language prediction. Take the phrase: The sky is blue. The string of words (i.e., data) has context. So as the state is updated, the string of data is updated from one iteration to the next, which provides context to predict blue. As just described RNNs have a memory component to aid in making predictions on sequenced data. However, the memory in the updated state of an RNN may be limited in how far it can look back, akin to short-term memory. When predicting sequenced data where a longer look back, akin to long term memory, is desired, tweaks to the RNNs just described may be used to accomplish this. A sentence, where the word to be predicted is unclear from the words closely preceding or surrounding, is again a simple example to explain: Mary speaks fluent French. It is unclear from the words closely preceding that French is the correct prediction; only that some language is the correct prediction, but which language? The correct prediction may lie in the context of words separated by a larger gap than the single string of words. Long Short Term Memory (LSTM) networks are a special kind of RNN, capable of learning these long(er)-term dependencies.

Figure 3:
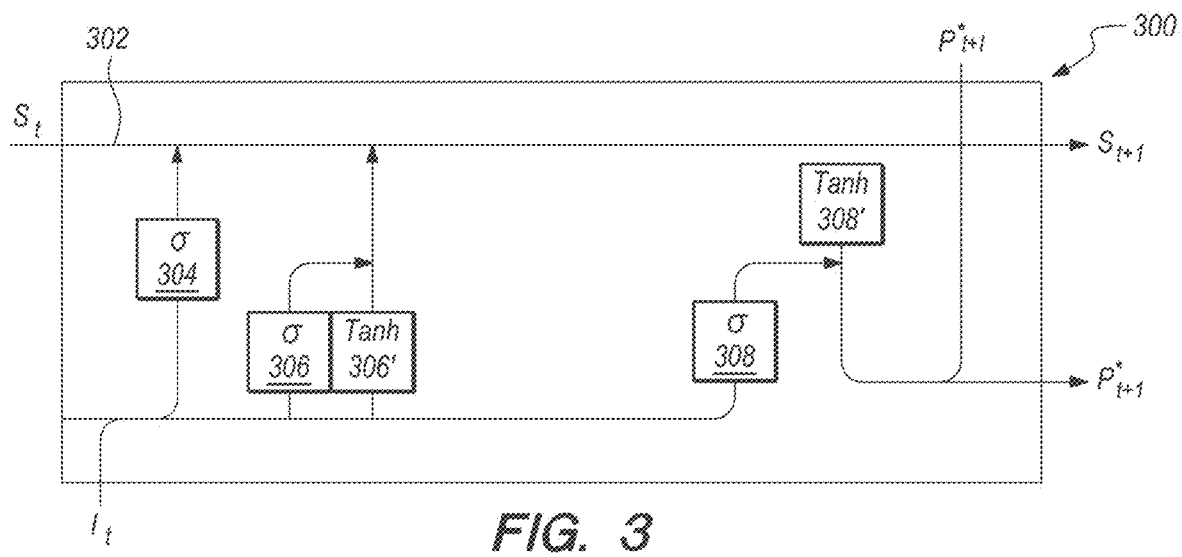
FIG. 3 depicts an alternative recurrent neural network that may be used in accordance with some embodiments as described herein.

As described above, RNNs have a relatively simple repeating structure, for example they may have a single layer with a nonlinear activation function (e.g., tan h or sigmoid). LSTMs similarly have a chain like structure, but (for example) have four neural network layers, not one. These additional neural network layers give LSTMs the ability to remove or add information to the state (S) by using structures called cell gates. Id. FIG. 3 shows a cell 300 for a LSTM RNN. Line 302 represents the cell state (S), and can be viewed as an information highway; it is relatively easy for information to flow along the cell state unchanged. Id. Cell gates 304, 306, and 308 determine how much information to allow through the state, or along the information highway. Cell gate 304 first decides how much information to remove from the cell state $S_t$, so-called forget-gate layer. Id. Next, cell gate 306 and 306' determines which information will be added to the cell state, and cell gate 308 and 308' determines what will be output from the cell state as prediction $P^*_{t+1}$. The information highway or cell state is now updated cell state $S_{t+1}$ for use in the next cell. LSTMs permits RNNs to have a more persistent or long(er)-term memory. LSTMs provide additional advantages to RNN based machine learning models in that output predictions take into account a context separated from the input data by longer space or time, depending on how the data is sequenced, than the simpler RNN structure.

In some embodiments utilizing an RNN, the primary and secondary time sequences may not be provided to the RNN as vectors at each time step. Instead, the RNN may be provided only the current value of the primary and secondary time sequence(s), along with the future values or aggregate functions of the secondary time sequence(s) within the prediction interval. In this manner, the RNN uses the persistent state vector to retain information about the previous values for use in making predictions Machine learning is well suited for continuous monitoring of one or multiple criteria to identify anomalies or trends, big and small, in input data as compared to training examples used to train the model. Accordingly, some embodiments described herein input a user's health-indicator data and optionally other-factor data into a trained machine learning model that predicts what a healthy person's health-indicator data would look like at the next time step and compares the prediction with the user's measured health-indicator data at the future time step. If the absolute value of the difference (e.g., loss as described below) exceeds a threshold, the user is notified his or her health-indicator data is not in a normal or healthy range. The threshold is a number set by the designer and, in some embodiments, may be changed by the user to allow a user to adjust the notification sensitivity. The machine learning model of these embodiments may be trained on health-indicator data alone or in combination with corresponding (in time) other-factor data from a population of healthy people, or trained on other training examples to suit the design needs for the model.

Data from health-indicators, like heart rate data, are sequenced data, and more particularly time sequenced data. Heartrate, for example and not by way of limitation, can be measured in a number of different ways, e.g., measuring electric signals from a chest strap or derived from a PPG signal. Some embodiments take the derived heartrate from the device, where each data point (e.g., heart rate) is produced at approximately equal intervals (e.g., 5s). But, in some cases and in other embodiments the derived heart rate is not provided in roughly equal time steps, for example because the data needed for the derivation is not reliable (e.g., PPG signal is unreliable because the device moved or from light pollution). The same may be said of obtaining the secondary sequence of data from motion sensors or other sensors used to collect the other-factor data.

The raw signal/data (electric signal from ECG, chest strap, or PPG signals) itself is a time sequence of data that can be used in accordance with some embodiments. For the purpose of clarity, and not by way of limitation, this description uses PPG to refer to the data representing the health-indicator. The skilled artisan will readily appreciate that either form of the data for the health-indicator, raw data, waveform or number derived from raw data or waveform, may be used in accordance with some embodiments described herein.

Machine learning models that may be used with embodiments described herein include by way of example not limitation Bayes, Markov, Gaussian processes, clustering algorithms, generative models, kernel and neural network algorithms. Some embodiments utilize a machine learning model based on a trained neural network, other embodiments utilize a recurrent neural network, and additional embodiments use LTSM RNNs. For the purpose of clarity, and not by way of limitation, recurrent neural networks will be used to describe some embodiments of the present description.

Figure 4A:
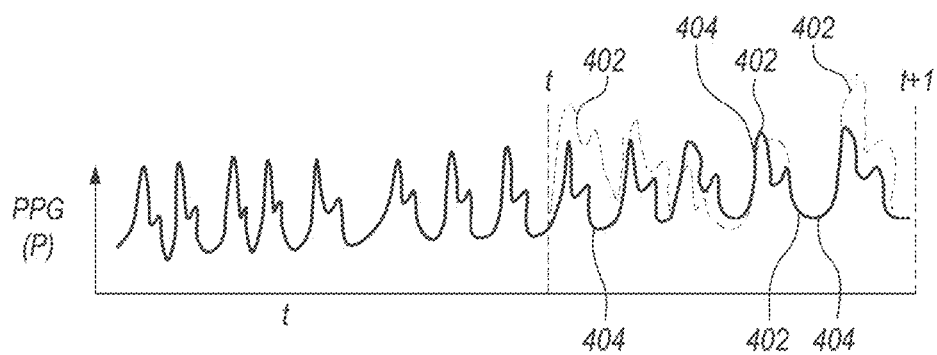
FIGS. 4A-4C depict hypothetical data plots to demonstrate application of some embodiments as described herein.
Figure 4B:
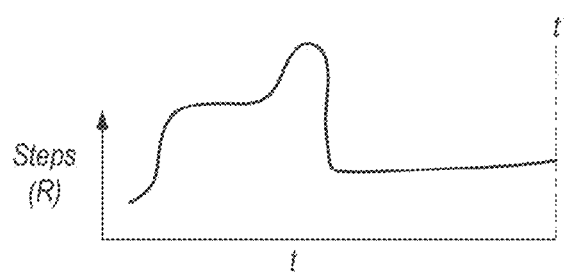
Figure 4C:
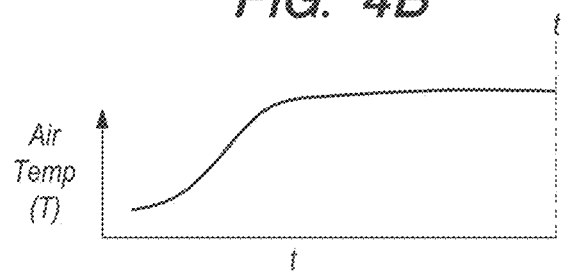

FIGS. 4A-4C show hypothetical plots against time for PPG (FIG. 4A), steps taken (FIG. 4B) and air temperature (FIG. 4C). PPG is an example of health-indicator data, where steps, activity level, and air temperature are examples other-factor data for other factors that may impact the health-indicator data. As will be appreciated by the skilled artisan, the other-data may be obtained from any of many known sources including without limitation accelerometer data, GPS data, a weight scale, user entry etc., and may include without limitation air temperature, activity (running, walking, sitting, cycling, falling, climbing stairs, steps etc.), BMI, weight, height, age etc. The first dotted line running vertically across all three plots represents time t at which the user data is obtained for input into a trained machined learning model (discussed below). The hashed plot lines in FIG. 4A represent predicted or probable output data 402, and solid lines 404 in FIG. 4A represent measured data. FIG. 4B is a hypothetical plot of number of a user's steps at various times, and FIG. 4C is a hypothetical plot of air temp at various times.

Figure 5A:
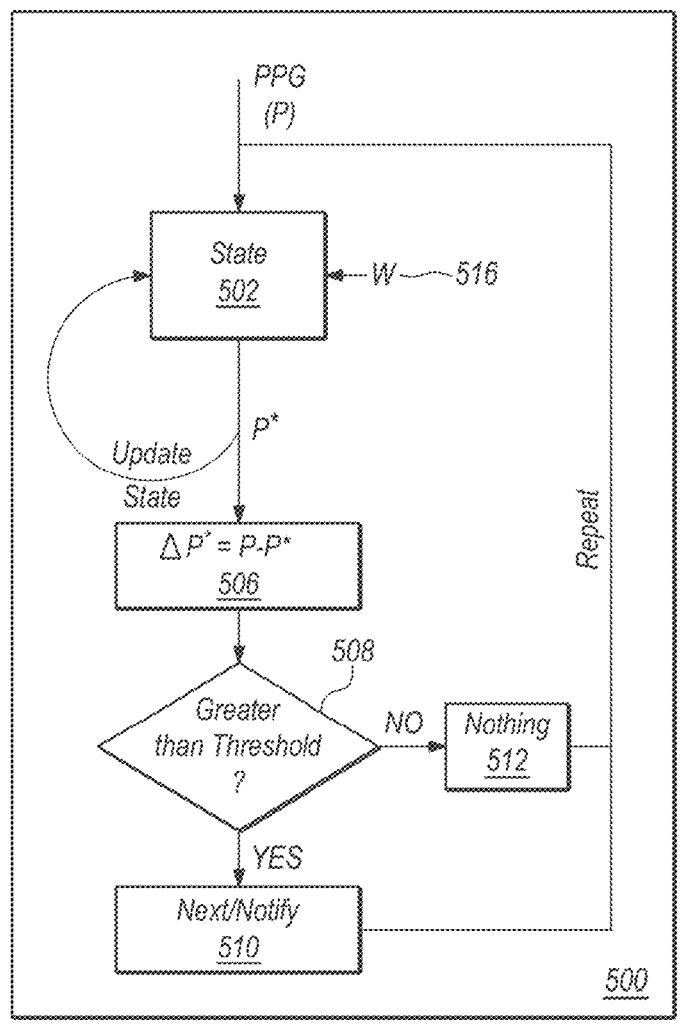
Figure 5B:
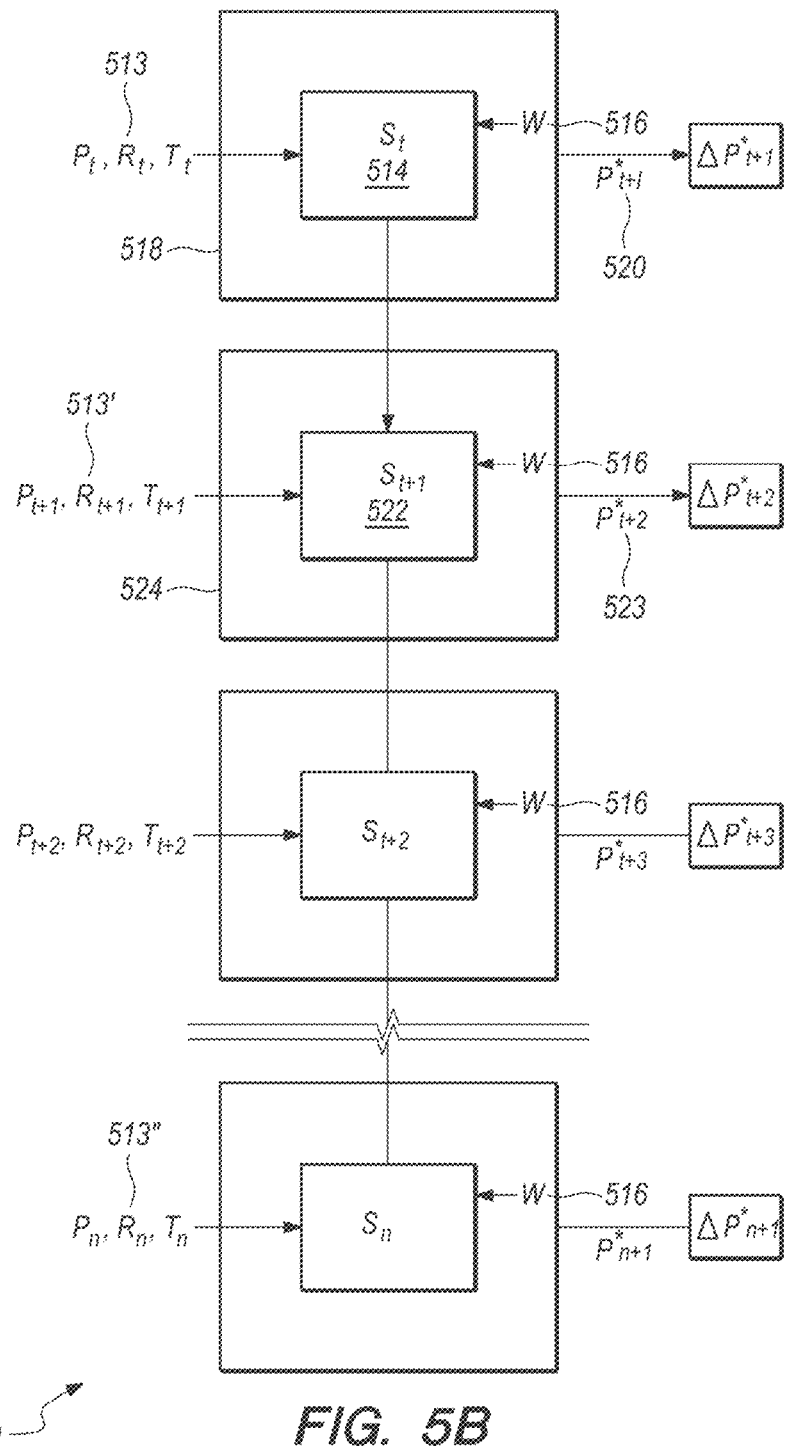

FIGS. 5A-5B depict a schematic for a trained recurrent neural network 500 to receive the input data depicted in FIGS. 4A-4C, i.e., PPG (P), steps (R) and air temperature (T). It is again emphasized that these input data (P, R and T) are merely examples of health-indicator data and other-factor data. It will also be appreciated that data for more than one health-indicator may be input and predicted, and more or less than two other-factor data may be used, where the choice depends on for what the model is being designed. It will be further appreciated by the skilled artisan that other-factor data is collected to correspond in time with the collection or measurement of the health-indicator data. In some cases, e.g. weight, other-factor data will remain relatively constant over certain periods of time.

FIG. 5A depicts trained neural network 500 as a loop. P, T and R are input into state 502 of RNN 500, where weights W are applied, and RNN 500 outputs predicted PPG 504 (P'). In step 506 the difference P-P* ($\Delta P^*$) is calculated, and at step 508 it is determined if $|\Delta P^*|$ is greater than a threshold. If yes, step 510 notifies/alerts the user his/her health-indicator is outside the bounds/threshold predicted as normal or predicted for a healthy person. The alert/notification/detection could be, for example and not by way of limitation, a suggestion to see/consult a doctor, a simple notification like a haptic feedback, request to take additional measurement like and ECG, or simple note without recommendation, or any combination thereof. If $|\Delta P^*|$ is less than or equal to the threshold, step 512 does nothing. In both steps 510 and 512 the process is repeated with new user data at the next time step. In this embodiment, the state is updated following the output of the predicted data, and may use the predicted data in updating the state.

In another embodiment, not shown, a primary sequence of heartrate data (e.g., derived from a PPG signal) and a secondary sequence of other-factor data are provided to the trained machine learning model, which may be an RNN a CNN, other machine learning models, or a combination of models. In this embodiment, the machine learning model is configured to receive as input at reference time t:

A. A vector ($V_H$) of length 300 of the last 300 health-indicator samples (e.g., heart rate in beats per minute) up to and including any health-indicator data at time t;

B. At least one vector ($V_O$) of length 300 containing the most recent other-factor data, e.g., step count, at the approximate time of each sample in Vii;

C. A vector ($V_{TD}$) of length 300 where the entry at index i, $V_{DT}(i)$, contains the time difference between the timestamps of health-indicator sample $V_H(i)$ and $V_H(i-1)$; and D. A scalar prediction interval other-factor rate $O_{rate}$ (step rate for example and not by way of limitation) representing the mean other-factor rate (e.g., step rate) measured over the time period from t to t+τ, where τ may be, for example and not by way of limitation, 2.5 minutes and is the future prediction interval.

The output of this embodiment may be, for example, a probability distribution characterizing the predicted heart rate measured over the time period from t to t+τ. In some embodiments, the machine learning model is trained with training examples that includes continuous time sequences of health-indicator data and other-factor data sequences. In one alternative embodiment the notification system assigns a timestamp to each predicted health-indicator (e.g., heart rate) distribution of t+τ/2, thus centering the predicted distribution within the predictive interval (τ). The notification logic, in this embodiment, then considers all samples within a sliding window (W) of length $W_L=2*(\tau)$ or 5 mins in this example and calculates three parameters:

1. Mean value of all health-indicator sequence data $\overline{H_W}$ within the time window
2. Mean value of all model predictions of the health-indicator $\overline{H^*_W}$, which predictions timestamp falls within the time window; and
3. Median value of the root-mean-square of each predicted health-indicator distribution within the time window ($RMS_W^H$); where
4. in one embodiment if $\overline{H_W} > \overline{H^*_W} + (\psi) \times RMS_W^H$ or $\overline{H_W} < \overline{H^*_W} - (\psi) \times RMS_W^H$ where ψ is a threshold, a notification is generated.

In this embodiment, an alert is generated when the measured health-indicator is more than a certain multiple of the standard deviation away from the mean of the predicted health-indicator values within a particular window W. The window W can be applied in a sliding fashion across the sequences of measured and predicted health-indicator values, with each window overlapping the previous window in time by a designer specified fraction, e.g., 0.5 mins.

The notification may take any number of different forms. For example, and not by way of limitation, it may notify the user to obtain an ECG and/or blood pressure, it may direct the computing system (e.g. wearable etc.) to automatically obtain an ECG or blood pressure (for example), it may notify the user to see a doctor, or simply inform the user the health-indicator data is not normal.

The choice of $V_{DT}$, in this embodiment, as input into the model is intended to allow the model to utilize information contained in the variable spacing between health-indicator data in $V_H$, where the variable spacing may result from algorithms deriving health-indicator data from less than consistent raw data. For example, heart rate samples are produced by the Apple Watch algorithm only when it has sufficiently reliable raw PPG data to output a reliable heart rate value, which results in irregular time gaps between heart rate samples. In similar fashion this embodiment utilizes the vector for other-factor data ($V_O$) with the same length as the other vectors to handle different and irregular sample rates between the primary sequence (health-indicator) and secondary sequence (other-factor). The secondary sequence, in this embodiment, is remapped or interpolated onto the same time points as the primary time sequence.

Furthermore, in some embodiments, the configuration of data from secondary time sequences presented as input to a machine learning model from a future prediction time interval (e.g. after t) may be modified. In some embodiments, the single scalar value containing the average other-factor data rate over the prediction interval, could be modified with multiple scalar values, e.g. one for each secondary time sequence. Or, a vector of values could be used over the prediction interval. Additionally, the prediction interval may itself be adjusted. A shorter prediction interval, for example, may provide faster response to changes and improved detection of events whose fundamental timescale is short(er), but may also be more sensitive to interference from sources of noise, like motion artifacts.

Similarly, the output prediction of the machine learning model itself does not need to be a scalar. For example some embodiments may generate a time series of predictions for multiple times t within the time interval between t and t+τ, and the alerting logic may compare each of these predictions with the measured value within the same time interval.

In this preceding embodiment, the machine learning model itself may comprise, for example, a 7-layer feed-forward neural network. The first 3 layers may be convolutional layers containing 32 kernels each with a kernel width of 24 and a stride of 2. The first layer may have as input the arrays $V_H$, $V_O$, and $V_{TD}$, in three channels. The final 4 layers may be fully-connected layers, all utilizing hyperbolic tangent activation functions except the last layer. The output of the third layer may be flattened into one array for input into the first fully connected layer. The final layer outputs 30 values parameterizing a Gaussian Mixture Model with 10 mixtures (mean, variance, and weight for each mixture). The network uses a skip connection between the first and third fully connected layers, such that the output of layer 6 is summed with the output of layer 4 to produce the input to layer 7. Standard batch normalization may be used on all layers but the last layer, with a decay of 0.97. The use of skip connections and batch normalization can improve the ability to propagate gradients through the network.

The choice of machine learning model may affect the performance of the system. The machine learning model configuration may be separated into two types of considerations. First is the model's internal architecture, meaning the choice of model type (convolutional neural network, recurrent neural network, random forests, etc. generalized non-linear regression), as well as the parameters that characterize the implementation of the model (generally, the number of parameters, and/or number of layers, number of decision trees, etc.). Second is the model's external architecture—the arrangement of data being fed into the model and the specific parameters of the problem the model is being asked to solve. The external architecture may be characterized in part by the dimensionality and type of data being provided as input to the model, the time range(s) spanned by that data, and the pre-or-post processing done on the data.

Generally speaking, the choice of external architecture is a balance between increasing the number of parameters and amount of information provided as input, which may increase the predictive power of the machine learning model, with the available storage and computational capacity to train and evaluate a larger model, and the availability of sufficient amounts of data to prevent overfitting.

Numerous variations of the model's external architecture discussed in some embodiments are possible. The number of input vectors, as well as the absolute length (number of elements) and time span covered, may be modified. It is not necessary that each input vector be the same length or cover the same span of time. The data does not need to be equally sampled in time—for example and not by way of limitation, one might provide a 6-hour history of heart rate data, in which data less than one hour before t is sampled at a rate of 1 Hz, data more than 1 hour before t but less than 2 hours before t is sampled at a rate of 0.5 Hz, and data older than 2 hours is sampled at a rate of 0.1 Hz, where t is the reference time.

FIG. 5B shows trained RNN 500 unrolled. Input data 513 ($P_t$, $R_t$, and $T_t$) is input into state-at-time t ($S_t$) 514 and trained weights 516 are applied. The output of cell ($C_t$) 518 is prediction-at-time t+1 ($P^*_{t+1}$) 520 and updated state $S_{t+1}$ 522. Similarly, in $C_{t+1}$ 524, input data ($P_{t+1}$, $R_{t+1}$, and $T_{t+1}$) 513' is input into $S_{t+1}$ 522 and trained weights 516 are applied and the output of $C_{t+1}$ 524 is $P^*_{t+2}$ 523. As noted above $S_{t+1}$ results from updating $S_t$, therefor $S_{t+1}$ has memory from $S_t$ from the operation in cell ($C_t$) 518 at the previous time step. This process continues for n-steps, where input data ($P_n$, $R_n$, and $T_n$) 513" is input into $S_n$ 530 and trained weights 516 are applied. The output of cell $C_t$ is prediction 532 $P^*_{n+1}$. Notably, trained RNNs apply the same weights throughout, but, and importantly, the states are updated from previous time steps giving RNNs the benefit of memory from a previous time step. The skilled artisan will appreciate that the order-in-time of inputting the dependent health-indicator data may vary and would still produce the desired result. For example, the measured health-indicator data from a previous time step (e.g., $P_{t-1}$) and the other-factor data from the current time step (e.g., $R_t$ and $T_t$) can be input into the state at the current time step ($S_t$), where the model predicts the health-indicator at the current time step $P^*_t$, which is compared to the measured health-indicator data at the present time step to determine if the user's health-indicator is normal or in a healthy range, as described above.

FIG. 5C shows an alternative embodiment of a trained RNN to determine whether a user's health-indicator sequenced data, PPG in our example, is in a band or threshold for a healthy person. The input data in this embodiment is a linear combination $I_t = \alpha_t P^*_t + (1-\alpha_t) P_t$, where $P^*_t$ is the predicted health-indicator value at time t and $P_t$ is the measured health-indicator at time t. In this embodiment α ranges from 0-1 nonlinearly as a function of loss (L), where the loss and a are discussed in more detail below. What is worth noting now is when α is near zero, the measured data $P_t$ is input into the network, and when α is near one, predicted data ($P^*_t$) is input into the network for making a prediction at the next time step. Other-factor data ($O_t$) at time t may optionally also be input.

$I_t$ and $O_t$ are input into state $S_t$ which, in some embodiments, outputs a probability distribution (β) of the predicted health-indicator data ($P^*_{t+1}$) at time step $$t+1 \left( \beta^{t+1}_{(P^*_{t+1})} \right),$$

where $\beta_{(P^*)}$ is the probability distribution function of predicted health-indicator (P*). In some embodiments, the probability distribution function is sampled to select a predicted health-indicator value at t+1 ($P^*_{t+1}$). As appreciated by the skilled artisan $\beta_{(P^*)}$ may be sampled using different methods depending on the goals of the network designer, which methods may include taking the mean value, max value or a random sampling of the probability distribution. Evaluating $\beta^{t+1}$ using the measured data at time t+1 provides the probability the state $S_{t+1}$ would have predicted for the measured data.

To illustrate this concept, FIG. 5D shows a hypothetical probability distribution for a range of hypothetical health-indicator data at time t+1. This function is sampled, for example at maximum probability 0.95, to determine a predicted health-indicator at time t+1 ($P^*_{t+1}$). The probability distribution ($\beta^{t+1}$) is also evaluated using the measured or actual health-indicator data ($P_{t+1}^{act.}$), and a probability is determined that the model would have predicted if the actual data had been input into the model. In this example $$\beta^{t+1}_{(P^{act}_{t+1})}$$

is 0.85.

A loss may be defined to help determine whether to notify a user his or her health status is not in a normal range as predicted by the trained machine learning model. The loss is chosen to model how close the predicted data is to the actual or measured data. The skilled artisan will appreciate many ways to define loss. In other embodiments described herein, for example, the absolute value of the difference between the predicted data and the actual data (|ΔP*|) is a loss. In some embodiments, the loss (L) may be L=−ln [$\beta_{(P)}$], where $$L_{t+1} = -\ln\left[\beta^{t+1}_{(P^{act}_{t+1})}\right].$$

L is a measure of how close the predicted data is to the measured or actual data. $\beta_{(P)}$ ranges from 0 to 1, where 1 means the predicted value and measured value are the same. Therefore, a low loss indicates the predicted value is probably the same as or close to the measured value; in this context it means the measured data looks like it comes from a healthy/normal person. In some embodiments, thresholds for L are set, e.g., L>5, where the user is notified the health-indicator data is outside the range considered healthy. Other embodiments may take an average of losses over a period of time and compare the average to a threshold. In some embodiments, the threshold itself may be a function of a statistical calculation of the predicted values or an average of the predicted values. In some embodiments, the following equation may be used to notify the user the health-indicator is not in a healthy range:

$$\left| \langle P_{range} \rangle - \langle P^*_{range} \rangle \right| > f\left( \sigma_{(\langle P^*_{range} \rangle)} \right)$$

$\langle P_{range} \rangle$ as determined by a method of averaging the measured health-indicator data over a time range $\langle P^*_{range} \rangle$ is determined by a method of averaging predicted health-indicator data over the same time range;

$$\sigma_{((P^*_{range}))}$$

is the median of the sequence of standard deviations derived from the network over the same time range; and $$f\left(\sigma_{((P^*_{range}))}\right)$$

is a function of the standard deviation evaluated at $P^*_{range}$ and may serve as the threshold.

The methods of averaging that may be used include, by way of example not limitation, average, arithmetic mean, median and mode. In some embodiments, outliers are removed so as not to skew the calculated number.

Referring back to the input data $(I_t=\alpha_t P^*_t+(1-\alpha_t)P_t)$ for the embodiment depicted in FIG. 5C, $\alpha_t$ is defined as a function of L and ranges from 0 to 1. For example, $\alpha(L)$ may be a linear function, or a non-linear function, or may be linear over some range of L and non-linear over a separate range of L. In one example, as shown in FIG. 5E, the function $\alpha(L)$ is linear for L between 0 and 3, quadratic for L between 3 and 13, and 1 for L greater than 13. For this embodiment, when L is between 0 and 3 (i.e., when the predicted health-indicator data and measured health-indicator data nearly match), the input data $I_{t+1}$ will be approximately the measured data $P_{t+1}$, as $\alpha-1$ will be near zero. When L is large, e.g., greater than 13, $\alpha(L)$ is 1, which makes the input data $I_{t+1}=P^*_{t+1}$, the predicted health-indicator at time t+1. When L is between 1 and 13, $\alpha(L)$ varies quadratically, and the relative contributions of predicted and measured health-indicator data to the input data will also vary. The linear combination of predicted health-indicator data and measured health-indicator data weighted by $\alpha(L)$ permits, in this embodiment, weighting the input data between predicted and measured data at any particular time step. In all these examples the input data may also include the other-factor data $(O_t)$. This is only one example of self-sampling, where some combination of predicted data and measured data are used as input to the trained network. The skilled artisan will appreciate many others may be used.

Figure 6:
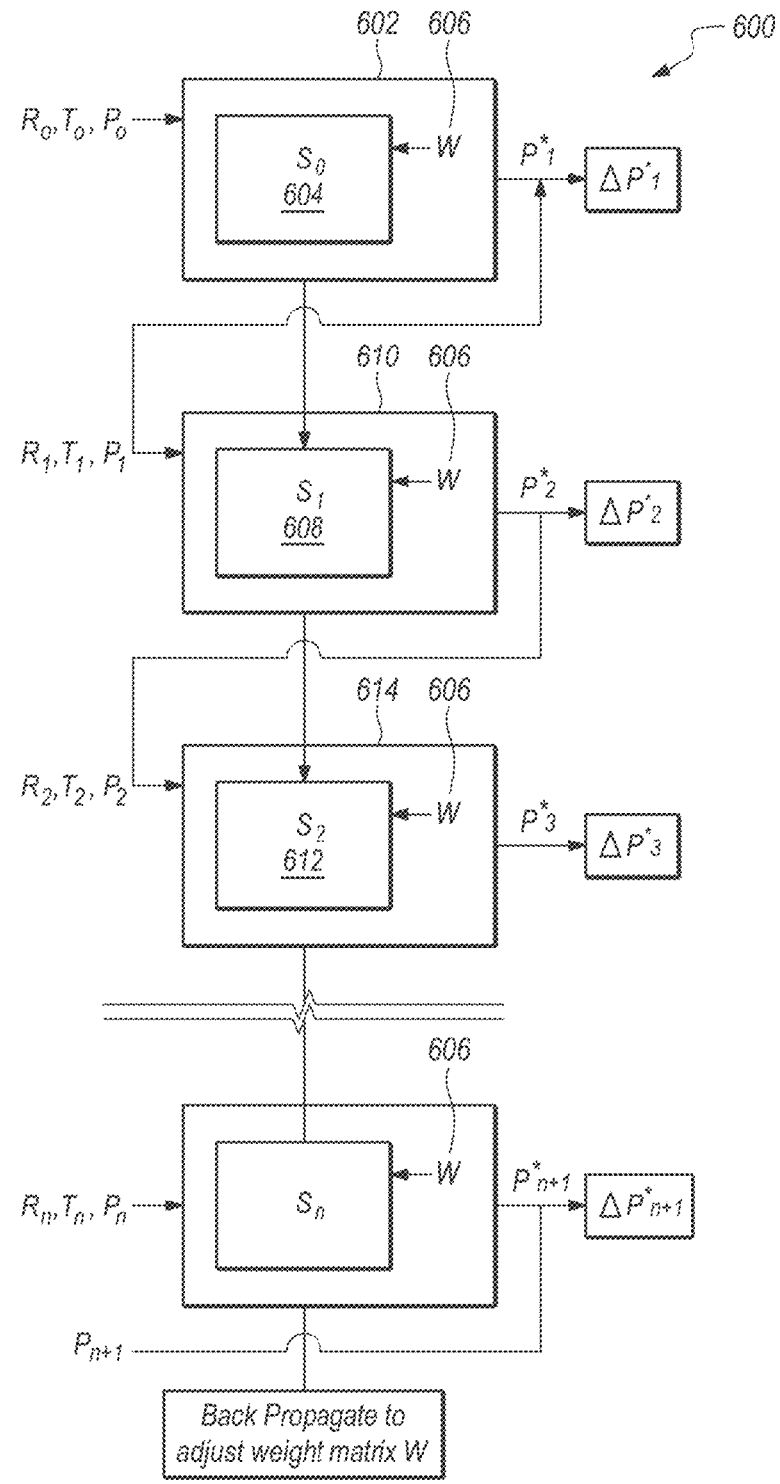
FIG. 6 depicts an unrolled recurrent neural network in accordance with some embodiments as described herein.

Machine learning models in embodiments use a trained machine learning model. In some embodiments, the machine learning models use a recurrent neural network, which requires a trained RNN. As an example, and not by way of limitation, FIG. 6 depicts an unrolled RNN to demonstrate training a RNN in accordance with some embodiments. Cell 602 has initial state $S_0$ 604 and weight matrix W 606. Step-rate data $R_0$, air temperature data $T_0$ and initial PPG data $P_0$ at the time step zero are input into state $S_0$, weight W is applied, and a predicted PPG $(P^*_1)$ at the first time step is output from cell 602, and $\Delta P^*_1$ is calculated using PPG obtained at time step 1 $(P_1)$. Cell 602 also outputs updated state at time step 1 608 $(S_1)$, which goes into cell 610. Step rate data $R_1$, air temperature data $T_1$ and PPG data $P_1$ at time step 1 are input into $S_1$, weight 606 W is applied, and a predicted PPG $(P^*_2)$ at the time step 2 is output from cell 610, and $\Delta P^*_2$ is calculated using PPG $(P_2)$ obtained at time step 2. Cell 610 also outputs updated state at time step 2 612 $(S_2)$, which goes into cell 614. Step rate data $R_3$, air temperature data $T_3$ and PPG data at time step 3 $(P_3)$ are input into $S_2$, weight 606 W is applied, and a predicted PPG $(P^*_3)$ at time step 3 is output from cell 614, and $\Delta P^*_3$ is calculated using PPG obtained at time step 3 $(P_3)$. This is continued until state at time-step-n 616 is output and $\Delta P^*_{n+1}$ is calculated. The $\Delta P^*$'s are used in back propagation to adjust the weight matrix, similar to the training of convolutional neural networks. However, unlike convolutional networks, the same weight matrix in recurrent neural networks is applied at each iteration; it is only modified in back propagation during training. Many training examples with health-indicator data and corresponding other-factor data are input into RNN 600 over and over until it converges. As discussed previously, LTSM RNNs may be used in some embodiments where the states of such networks provide a longer term contextual analysis of input data, which may provide better prediction when the network learns long(er)-term correlations. As also mentioned and the skilled artisan will readily appreciate other machine learning models will fall within the scope of embodiments described herein, and may include by way of example not limitation CNN or other feed-forward networks.

Figure 7A:
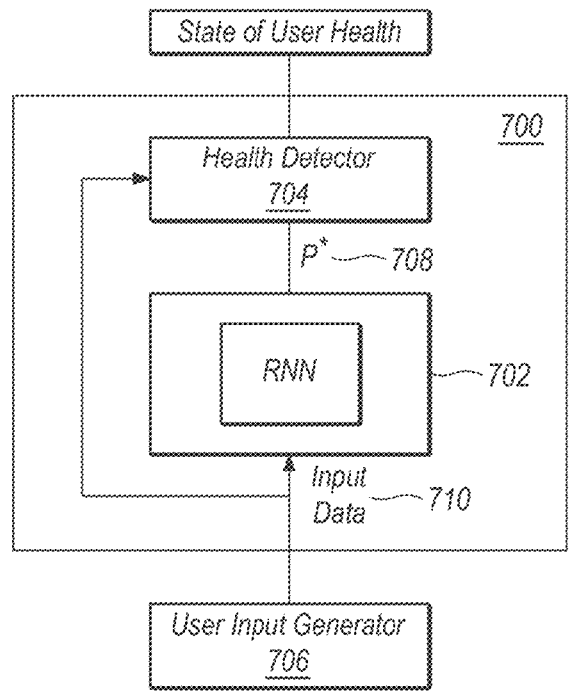
FIGS. 7A-7B depicts systems and devices in accordance with some embodiments as described herein.

FIG. 7A depicts a system 700 that predicts whether a user's measured health-indicators are within or outside a threshold of normal for that of a healthy person under similar other-factors. System 700 has machine learning model 702 and health detector 704. Embodiments for machine learning model 702 include a trained machine learning model, a trained RNN, CNN or other feed forward network for example (and not by way of limitation). The trained RNN, other network or combination of networks may be trained on training examples from a population of healthy people from whom health-indicator data and corresponding (in time) other-factor data has been collected. Alternatively, the trained RNN, other network or combination of networks may be trained on training examples from a particular user, making it a personalized trained machine learning model. The skilled artisan will appreciate training examples from different populations may be selected depending on the use or design for the trained network and system in general. The skilled artisan will also readily appreciate that the health-indicator data in this and other embodiments may be one or more health-indicators. For example, and not by way of limitation, one or more of PPG data, heartrate data, blood pressure data, body temperature data, blood oxygen concentration data and the like could be used to train the models and to predict the health of a user. Health detector 704 uses prediction 708 from machine learning model 702 and input data 710 to determine whether a loss, or other metric determined by analyzing the predicted output with the measured data, exceeds a threshold considered normal and thus unhealthy. System 700 then outputs a notification or the state of a user's health. This notification may take many forms as discussed herein. Input generator 706 continuously obtains data with a sensor (not shown) from a user wearing or in contact with the sensor, where the data represents one or more health-indicators of the user. Corresponding (in time) other-factor data may be collected by another sensor or acquired through other means as described herein or as readily apparent to the skilled artisan.

Input generator 706 may also collect data to determine/calculate other-factor data. Input generator, for example and not by way of limitation, may include a smart watch, wearable or mobile device (e.g., Apple Watch® or FitBit® smart phone, tablet or laptop computer), a combination of smart watch and mobile device, a surgically implanted device with the ability to transmit data to a mobile device or other portable computing device, or a device on a cart in a medical care facility. Preferably user input generator 706 has a sensor (e.g., PPG sensor, electrode sensor) to measure data related to one or more health-indicators. The smart watch, tablet, mobile phone or laptop computer of some embodiments may carry the sensor or the sensor may be remotely placed (surgically embedded, contacted to the body remote from the mobile device, or some separate device) where, in all these cases, the mobile device communicates with the sensor in order to gather health-indicator data. In some embodiments, system 700 may be provided on the mobile devices alone, in combination with other mobile devices, or in combination with other computing systems via communication through a network through which these devices may communicate. For example, and not by way of limitation, system 700 may be a smart watch or wearable with machine learning model 702 and health detector 704 located on the device, e.g., the memory of the watch or firmware on the watch. The watch may have user input generator 706 and communicate with other computing devices (e.g. mobile phone, tablet, lap top computer or desk top computer) via direct communication, wireless communication (e.g., WiFi, sound, Bluetooth, etc.) or through a network (e.g., internet, intranet, extranet etc.) or a combination thereof, where trained machine learning model 702 and health detector 704 may be located on the other computing devices. The skilled artisan will appreciate that any number of configurations of system 700 may be utilized without exceeding the scope of embodiments described herein.

Figure 7B:
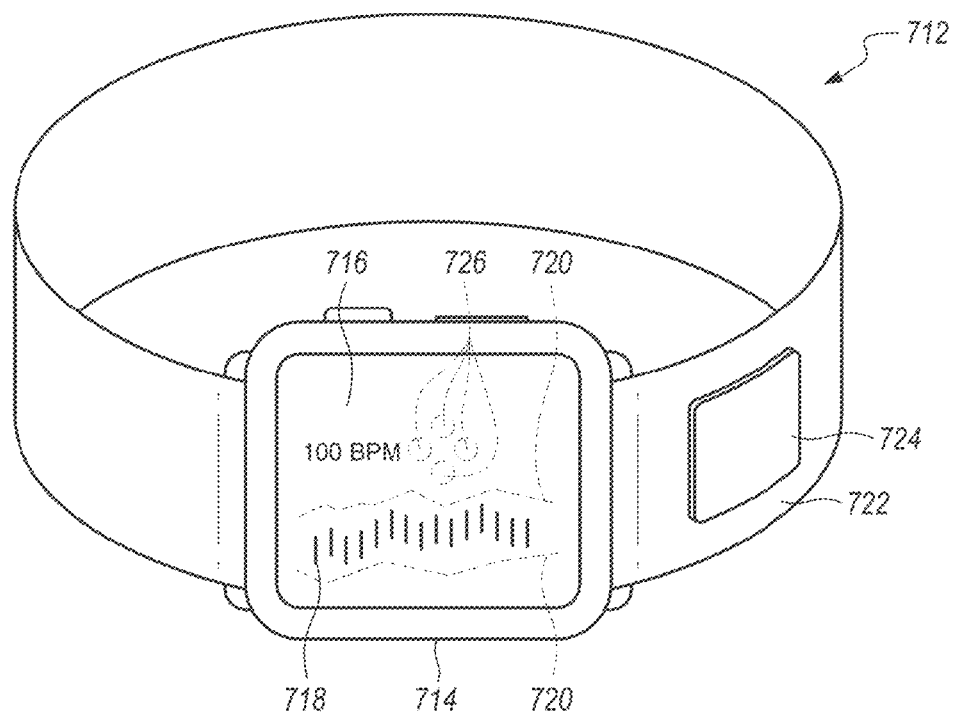

Referring to FIG. 7B smart watch 712, in accordance with an embodiment, is depicted. Smart watch 712 includes watch 714 which contains all the circuitry and microprocessors, and processing devices (not shown) known to the skilled artisan. Watch 714 also includes display 716, on which a user's health-indicator data 718 may be displayed, in this example heart rate data. Also displayed on display 716 may be the predicted health-indicator band 720 for the normal or the healthy population. In FIG. 7B the user's measured heart rate data does not exceed the predicted healthy band, so in this particular example no notification would be made. Watch 714 may also include watch band 722, and high-fidelity sensor 724, for example an ECG sensor. Alternatively, watch band 722 may be an expandable cuff to measure blood pressure. Low-fidelity sensors 726 (shown in shadow) are provided on the back of watch 714 to collect user health-indicator data, such as PPG data, which can be used to derive heart rate data or other data like blood pressure, for example. Alternatively, as will be appreciated by the skilled artisan, a fitness band may be used in some embodiments, such as FitBit or Polar, where the fitness bands have similar processing power and other-factor measurement devices (e.g., ppg and accelerometers).

Figure 8:
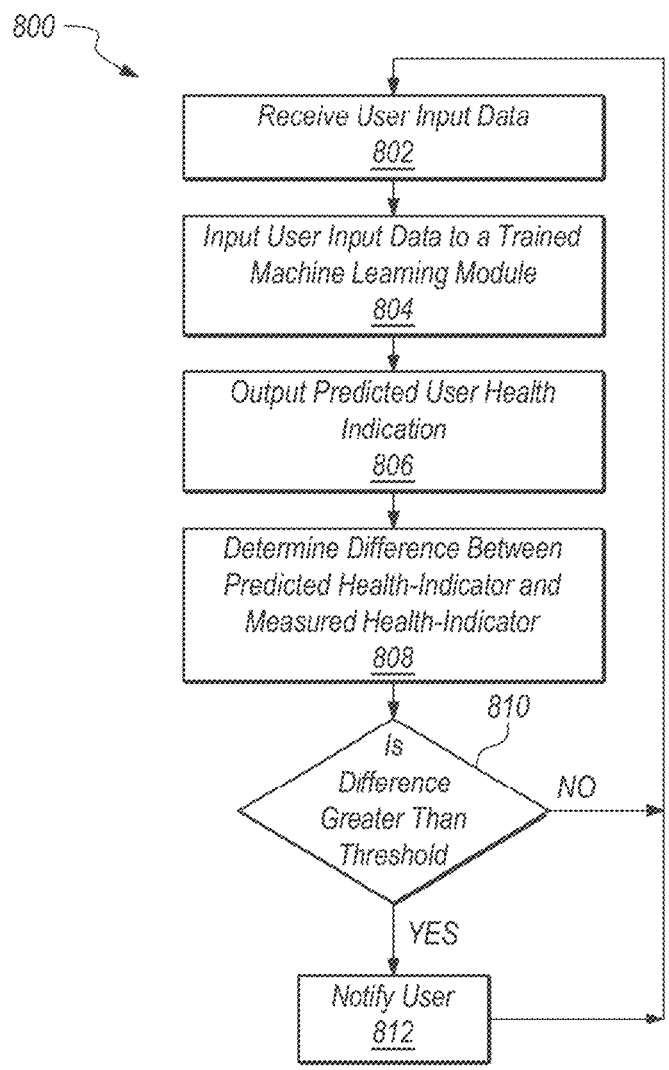
FIG. 8 depicts a method in accordance with some embodiments as described herein.

FIG. 8 depicts an embodiment of a method 800 for continuously monitoring a user's health status. Step 802 receives the user input data, which may include data for one or more health-indicators (aka primary sequence of data) and corresponding (in time) data for other-factors (aka secondary sequence of data). Step 804 inputs the user data into a trained machine learning model, which may include a trained RNN, CNN, other feed-forward network as described herein or other neural network known to the skilled artisan. In some embodiments, the health-indicator input data may be one or a combination of predicted health-indicator data and measured health-indicator data, e.g., a linear combination, as described in some embodiments herein. Step 806 outputs data for one or more predicted health-indicators at a time step, which outputs may include, by way of example not limitation, a single predicted value, a probability distribution as a function of predicted values. Step 808 determines a loss based on the predicted health-indicator, where, for example and not by way of limitation, the loss may be a simple difference between predicted and measured health-indicators, or some other appropriately selected loss function (e.g. negative log of a probability distribution evaluated at the value for the measured health-indicator). Step 810 determines if the loss exceeds a threshold considered normal or unhealthy, where the threshold may be, for example and not by way of limitation, a simple number picked by the designer, or a more complex function of some parameter related to the prediction. If greater than the threshold, step 812 notifies the user that his or her health indicator exceeds a threshold considered normal or healthy. The notification, as described herein, may take many forms. In some embodiments, this information may be visualized to the user. For example, and not by way of limitation, the information can be displayed on a user interface such as a graph that shows (i) measured health-indicator data (e.g., heart rate) and other-factor data (e.g., step count) as a function of time, (ii) a distribution of predicted health-indicator data (e.g., predicted heart rate values) generated by the machine learning model. In this way, the user can visually compare the measured data points to the predicted data points and determine by visual inspection whether their heart rate, for example, falls into the range expected by the machine learning model.

Some embodiments described herein have mentioned using a threshold to determine whether to notify a user or not. In one or more of these embodiments, the user may change the threshold to adjust or tune the system or method to more closely match the user's personal health knowledge. For example, if the physiological indicator used is blood pressure and the user has higher blood pressure, then embodiments may frequently alert/notify the user that his health-indicator is outside normal or healthy range from a model trained on a healthy population. Thus, certain embodiments permit the user to increase the threshold value so the user is not notified so frequently that his/her health-indicator data exceeds what is considered normal or healthy.

Some embodiments preferably use the raw data for the health-indicators. If the raw data is processed to derive a specific measurement, e.g., heart rate, this derived data may be used in accordance with embodiments. In some situations, the provider of a health monitoring apparatus does not have control of the raw data, rather what is received is processed data in the form of a calculated health-indicator, e.g., heart rate or blood pressure. As will be appreciated by the skilled artisan, the form of the data used to train a machine learning model should match the form of the data collected from the user and input into the trained model, otherwise the predictions could prove erroneous. For example, the Apple Watch gives heart rate measurement data at unequal time steps, and does not provide raw PPG data. In this example, a user wears an Apple Watch that outputs heart rate data in accordance with Apple's PPG processing algorithm with heart rate data at unequal time steps. The model is trained on this data. Apple deciding to change its algorithm for providing the heart rate data may render the model trained on data from the previous algorithm obsolete to use on data input from the new algorithm. To account for this potential issue, some embodiments resample the irregularly spaced data (heart rate, blood pressure data, or ECG data etc.) onto a regularly spaced grid and sample from regularly spaced grid when collecting data to train the model. If Apple, or other supplier of data, changes its algorithm, the model needs only to be retrained on newly collected training examples, but the model does not need to be reconstructed to account for the algorithm change.

In a further embodiment, the trained machine learning model may be trained on the user's data, resulting in a personalized trained machine learning model. This trained personalized machine learning model can be used in place of or in combination with the machine learning models trained on a healthy population of people described herein. If used by itself, a user's data is input into the personalized trained machine learning model, which would output a prediction of that individual's health-indicator in the next time step that is normal for that user, which is then compared with the actual/measured data from the next time step in a manner consistent with embodiments described herein to determine whether the user's health-indicators had differed by some threshold from what is predicted normal for that user. In addition, this personalized machine learning model could be used in combination with the machine learning model trained on training examples from a population of healthy people to generate predictions and associated notifications as related to both what is predicted normal for that individual user and predicted normal for the healthy population of people.

Figure 9A:
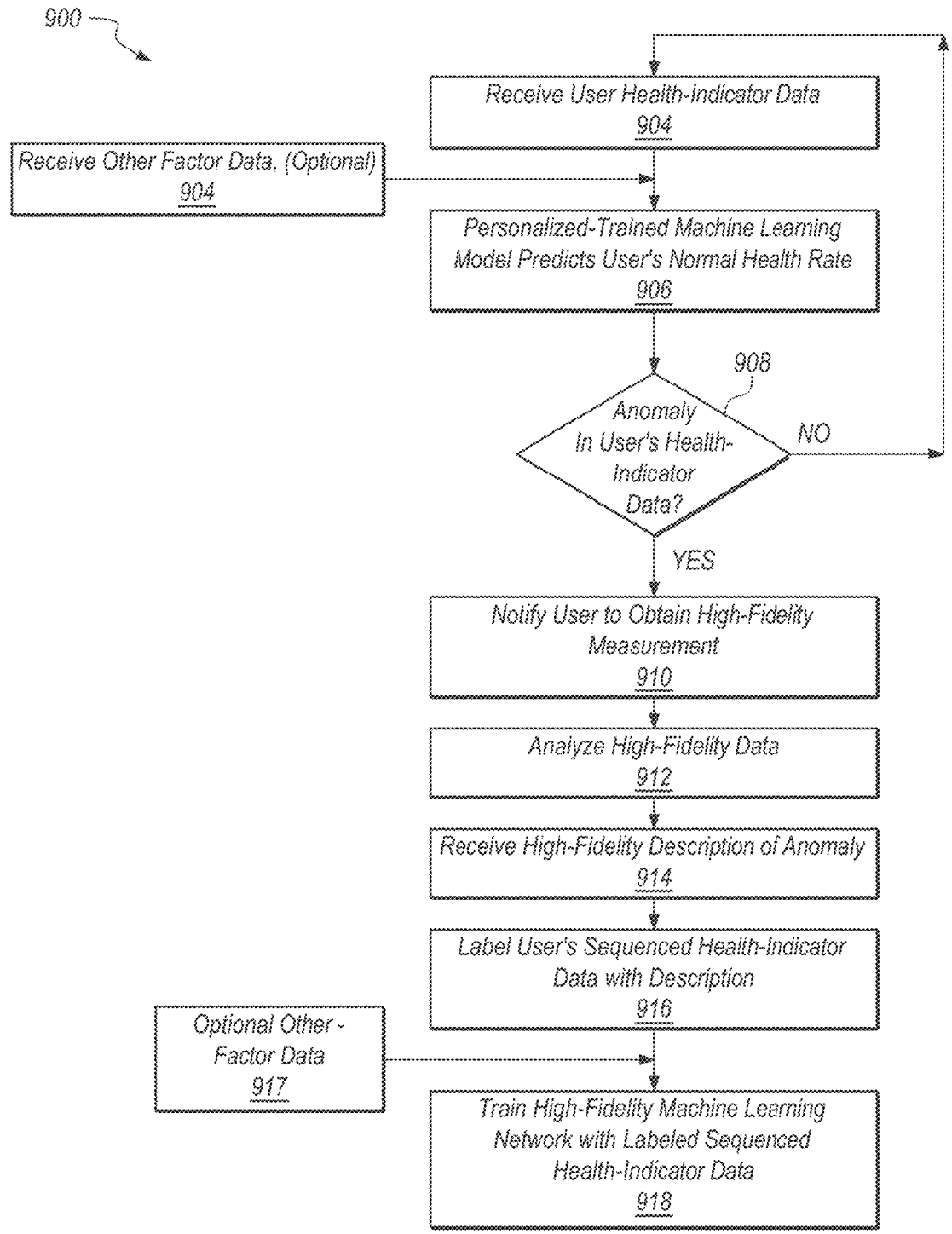
FIGS. 9A-9B depicts a method in accordance with some embodiments as described herein and a hypothetical plot of heartrate versus time to demonstrate one or more embodiments.
Figure 9B:
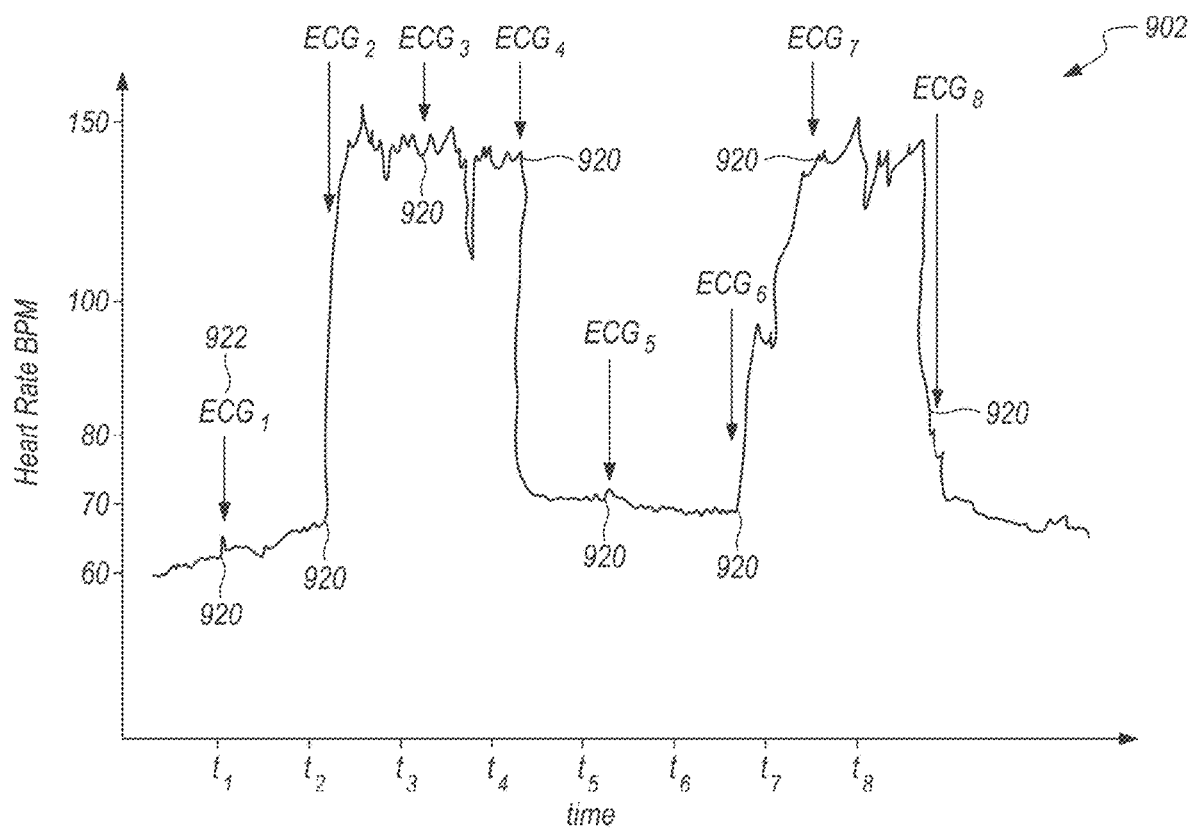

FIG. 9A depicts a method 900 in accordance with another embodiment, and FIG. 9B shows a hypothetical plot 902 of heart rate (by way of example not limitation) as a function of time for the purpose of explanation. Step 904 (FIG. 9A) receives user heart rate data (or other health-indicator data) and, optionally, corresponding (in time) other-factor data, and inputs this data into a personalized-trained machine learning model. In some embodiments, the personalized-trained model is trained on the user's individual health-indicator data and, optionally, corresponding (in time) other-data as described herein. Thus, in step 906 the personalized-trained machine learning model predicts normal heart rate data for that individual user under conditions of the other-factor(s), and step 908 identifies aberrations or anomalies in the user's health-indicator data as compared to what is predicted as normal for that particular user. Some embodiments receive the user's health-indicator data from a wearable device (e.g., Apple Watch, smart watch, FitBit®, etc.) on the user, or from another mobile device (e.g., tablet, computer, etc.) in communication with a sensor on the user (e.g., Polar® strap, PPG sensor etc.), which is discussed throughout this description.

A loss may be defined to help determine whether to notify a user, in step 908, that the user's measured data is anomalous to what is predicted as normal for that particular user. The loss is chosen to model how close the prediction is to the actual or measured data. The skilled artisan will appreciate many ways to define loss. In other embodiments described herein and equally applicable here, for example, the absolute value of the difference between the predicted value and the absolute value $|\Delta P^*|$ is a form of a loss. In some embodiments, the loss (L) may be $L=-\ln[\beta_{(P)}]$, where $$L_{t+1} = -\ln\left[\beta_{(P_{t+1}^{act})}^{t+1}\right].$$

L, generally, is a measure of how close the predicted data is to the measured data. $\beta_{(P)}$, the probability distribution in this example, ranges from 0 to 1, where 1 means the predicted data and measured data are the same. Therefore, a low loss, in some embodiments, indicates the predicted data are probably the same as or close to the measured data. In some embodiments, thresholds for L are set, e.g., L>5, where the user is notified an anomalous condition exists from that predicted for that particular user. This notification may take many forms, as described elsewhere herein. As also described elsewhere herein, other embodiments may take an average of losses over a period of time and compare the average to a threshold. In some embodiments, as described in more detail elsewhere herein, the threshold itself may be a function of a statistical calculation of the predicted data or an average of the predicted data. Loss has been described in more detail elsewhere herein, and for the sake of brevity will not be discussed further here. The skilled artisan will also appreciate the input and predicted data may be scalar values, or segments of data over a time period. For example, and not by way of limitation, a system designer may be interested in 5-minute data segments, and would input all the data prior to time t and all other-data for t+5 min, predict the health-indicator data for t+5 mins and determine a loss between measured health-indicator data for the t+5 min segment against the predicted health-indicator data for the t+5 min segment.

Step 908 determines if an anomaly is present or not. As discussed this may be determined if the loss exceeds a threshold. As previously described, the threshold is set by choice of the designer and based on the purpose of the system being designed. In some embodiments the threshold may be modified by the user, but preferably not so in this embodiment. If an anomaly is not present, the process is repeated at step 904. If an anomaly is present, step 910 notifies or alerts the user to obtain a high-fidelity measurement, an ECG or blood pressure measurement for example and not by way of limitation. In step 912, the high-fidelity data is analyzed by an algorithm, a health professional or both and is described as normal or not normal, and if not normal some diagnosis may be assigned, e.g., AFib, tachycardia, bradycardia, atrial flutter, or high/low blood pressure depending on the high-fidelity measurement obtained. It is noted for clarity, that notification to record high-fidelity data is equally applicable and possible in other embodiments, and in particular embodiments using general models described above. The high-fidelity measurement, in some embodiments, may be obtained directly by the user using a mobile monitoring system, such as ECG or blood pressure systems, which may be associated with the wearable device in some embodiments. Alternatively, the notification step 910 causes automatic acquisition of the high-fidelity measurement. For example, the wearable device may communicate with a sensor (hard-wired or via wireless communication) and obtain ECG data, or it may communicate with a blood pressure cuff-system (e.g., wrist band of a wearable or an armband cuff) to automatically obtain a blood pressure measurement, or it may communicate with an implanted device such as a pace maker or ECG electrodes. Systems for remotely obtaining an ECG are provided, for example, by AliveCor, Inc., such systems include (without limitation) one or more sensors contacting the user in two or more locations, where the sensor collects electrical cardiac data that is transmitted, either wired or wirelessly, to a mobile computing device, where an app generates an ECG strip from the data, which can be analyzed by algorithms, a medical professional or both. Alternatively, the sensor may be a blood pressure monitor, where the blood pressure data are transmitted, either wired or wirelessly, to the mobile computing device. The wearable itself may be a blood pressure system having a cuff with ability to measure health-indicator data and optionally with an ECG sensor similar to that described above. The ECG sensor may also include an ECG sensor such as that described in co-owned U.S. Provisional Application No. 61/872,555, the contents of which is incorporated herein by reference. The mobile computing device may be, for example and not by way of limitation, a computer tablet (e.g., iPad), smart phone (e.g., iPhone®), wearable (e.g., Apple Watch) or a device (maybe mounted on a cart) in a healthcare facility. The mobile computing device could be, in some embodiments, a laptop computer or a computer in communication with some other mobile device. The skilled artisan will appreciate that a wearable or smartwatch will also be considered mobile computing devices in terms of the capabilities provided in the context of embodiments described herein. In the case of a wearable, the sensor may be placed on the band of the wearable where the sensor may transmit the data wirelessly or by wire to the computing device/wearable, or the band may also be a blood pressure monitoring cuff, or both as previously described. In the case of a mobile phone, the sensor may be pads attached to or remote from the phone, where the pads sense electrical cardiac signals and wirelessly or by hardwire communicate the data to the wearable or other mobile computing device. More detailed descriptions for some of these systems are provided in one or more of U.S. Pat. Nos. 9,420,956; 9,572,499; 9,351,654; 9,247,911; 9,254,095; and 8,509,882 and one or more of US Patent Application Publication Numbers 2015/0018660; 2015/0297134; and 2015/0320328, all of which are incorporated herein in their entirety and for all purposes. Step 912 analyzes the high-fidelity data and provides a description or diagnosis, as previously described.

In step 914, diagnosis or categorization of the high-fidelity measurement is received by a computing system, which may be in some embodiments the mobile or wearable computing system used to collect the user's heart rate data (or other health-indicator data), and in step 916 the low-fidelity health-indicator data sequence (heart rate data in this example) is labeled with the diagnosis. In step 918, the labeled user's low-fidelity data sequence is used to train a high-fidelity machine learning model, and optionally other-factor data sequence is also provided to train the model. The trained high-fidelity machine learning model, in some embodiments, has the capability to receive measured low-fidelity health-indicator data sequence (e.g., heart rate data or PPG data) and optionally other-factor data and give a probability or predict or diagnose or detect when a user is experiencing an event typically diagnosed or detected using high-fidelity data. The trained high-fidelity machine learning model is able to do this because it has been trained on user's health-indicator data (and optionally other-factor data) labeled with diagnoses of the high-fidelity data. Thus, the trained model has the ability to predict when a user is having an event associated with one or more of the labels (e.g., Afib, high blood pressure etc.) solely based on measured low-fidelity health-indicator input data sequence, e.g. heart rate or ppg data (and optionally other-factor data). As the skilled artisan will appreciate, the training of the high-fidelity model can take place on the user's mobile device, remote from the user's mobile device, a combination of the two, or in a distributed network. For example, and not by way of limitation, the user's health-indicator data could be stored in a cloud system, and this data can be labeled in the cloud using the diagnosis from step 914. The skilled artisan will readily appreciate any number of ways and manners to store, label and access this information. Alternatively, a global trained high-fidelity model could be used, which would be trained on labeled training examples from a population of people experiencing these conditions typically diagnosed or detected with high-fidelity measurements. These global training examples would provide low-fidelity data sequences (e.g., heart rate) labeled with conditions diagnosed using a high-fidelity measurement (e.g., Afib called from a ECG by a medical professional or an algorithm).

Referring now to FIG. 9B, plot 902 shows a schematic of heart rate plotted as a function of time. Aberrations 920 from the user's normal heart rate data occurred at times $t_1$, $t_2$, $t_3$, $t_4$ $t_5$, $t_6$, $t_7$, $t_8$. Normal, as described above, means that the predicted data for this particular user was within a threshold of the measured data, where the aberrations are outside the threshold. At aberrations from normal some embodiments prompt the user to obtain a more definitive or high-fidelity reading, by way of example not limitation an ECG reading, identified as $ECG_1$, $ECG_2$, $ECG_3$, $ECG_4$, $ECG_5$, $ECG_6$, $ECG_7$, $ECG_8$. As described above the high-fidelity reading could be automatically obtained, the user may obtain it, and it could be things other than an ECG, e.g., blood pressure. High-fidelity readings are analyzed by algorithm, health professional or both to identify the high-fidelity data as normal/abnormal and to further identify/diagnose abnormal, AFib for example and not by way of limitation. This information is used to label the health-indicator data (e.g., heart rate or PPG data) at the point(s) of anomaly 920 in the user's sequenced data.

The distinction between high-fidelity and low-fidelity data is one where high-fidelity data or measurements are typically used to make a determination, detection or diagnosis, where low-fidelity data cannot readily be used for such. For example, an ECG scan may be used to identify, detect or diagnose arrhythmias, whereas heart rate or PPG data do not typically provide this capability. As the skilled artisan will appreciate, the description herein relating to machine learning algorithms (e.g., Bayes, Markov, Gaussian processes, clustering algorithms, generative models, kernel and neural network algorithms) apply equally to all embodiments described herein.

In some situations, users remain asymptomatic despite that issues may be present, and even if symptoms present it may be impractical to obtain the high-fidelity measurement necessary to make a diagnosis or detection. For example, and not by way of limitation, arrhythmias particularly AF may not present and even when symptoms do present it is notoriously difficult to record an ECG at that moment, and without expensive, bulky and sometimes invasive monitoring devices it is incredibly difficult to continuously monitor the user. As discussed elsewhere herein, it is important to understand when a user experiences AF because AF, at a minimum, may be a causal factor in stroke among other serious conditions. Similarly, and as discussed elsewhere, AF burden may have similar import. Some embodiments allow for continuous monitoring of arrhythmias (e.g., AF) or other serious conditions using only the continuous monitoring of low-fidelity health-indicator data, such as heart rate or ppg along with optional other-factor data.

Figure 10:
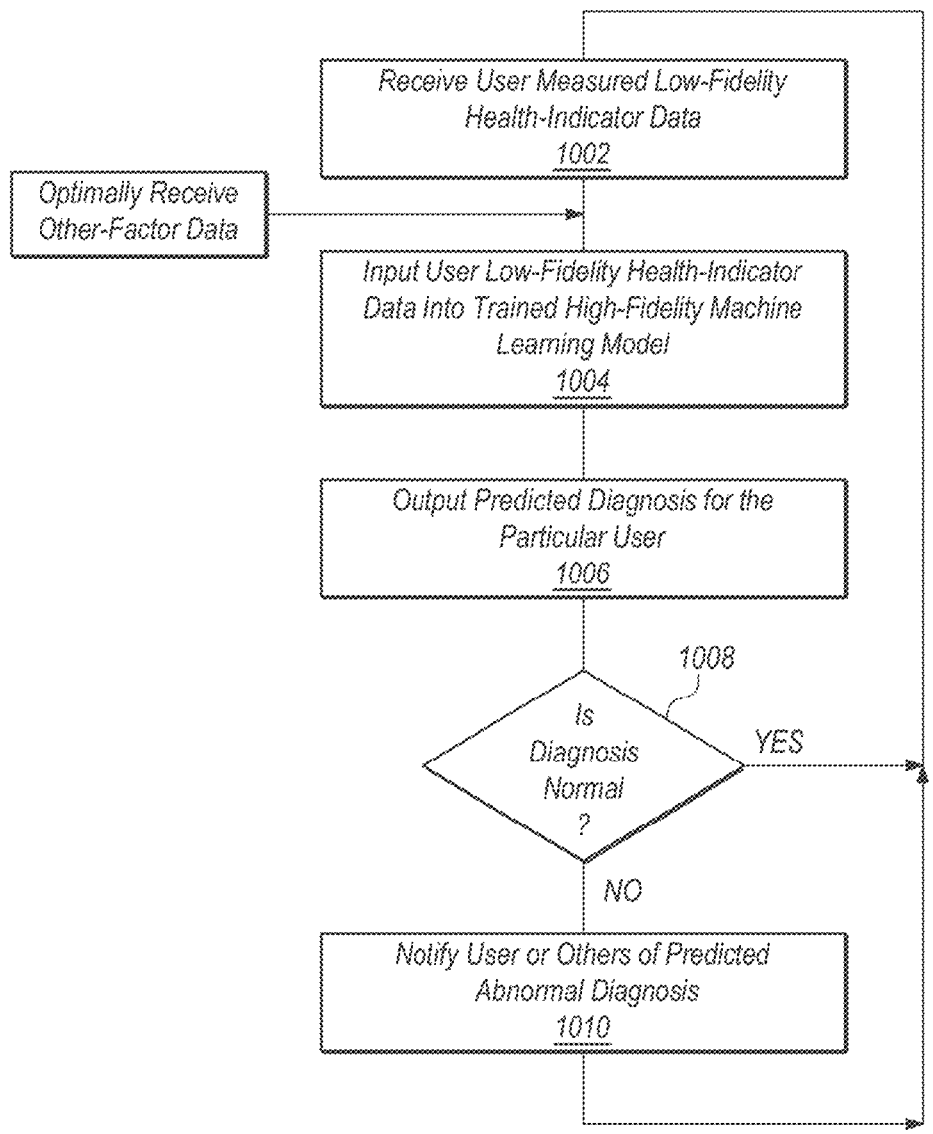
FIG. 10 depicts a method in accordance with some embodiments as described herein.

FIG. 10 depicts a method 1000 in accordance with some embodiments of health monitoring systems and methods. Step 1002 receives measured or actual user low-fidelity health-indicator data (e.g., heart rate or PPG data from a sensor on a wearable), and optionally receives corresponding (in time) other-factor data, which may impact the health-indicator data as described herein. As discussed elsewhere herein the low-fidelity health-indicator data may be measured by a mobile computing device, such as a smart watch, other wearable, or computer tablet. In step 1004, the user's low-fidelity health-indicator data (and optionally the other-factor data) is input into a trained high-fidelity machine learning model, which, in step 1006, outputs a predicted identification or diagnosis for the user based on the measured low-fidelity health-indicator data (and optionally corresponding (in time) other-factor data). Step 1008 asks if the identification or diagnosis is normal, which, if yes, the process starts over. If the identification or diagnosis is not normal, step 1010 notifies the user of the problem or detection. Optionally, the system, method or platform may be set up to notify any combination of the user, family, friends, healthcare professionals, emergency 911, or the like. Which of these people are notified may depend on the identification, detection or diagnosis. If the identification, detection or diagnosis is life threatening, then certain people may be contacted or notified that may not be notified if the diagnosis is not life threatening. In addition, in some embodiments, the measured health-indicator data sequence is input into the trained high-fidelity machine learning model and the amount of time a user is experiencing an abnormal event (e.g., difference between onset and cessation of the predicted abnormal event) is calculated, permitting a better understanding of the abnormal burden on the user. In particular, AF burden may be highly important to understand in preventing stroke and other serious conditions. Thus, some embodiments allow continuous monitoring of abnormal events with a mobile computing device, a wearable computing device or other portable device capable of only acquiring low-fidelity health-factor data, and optionally other-factor data.

Figure 11:
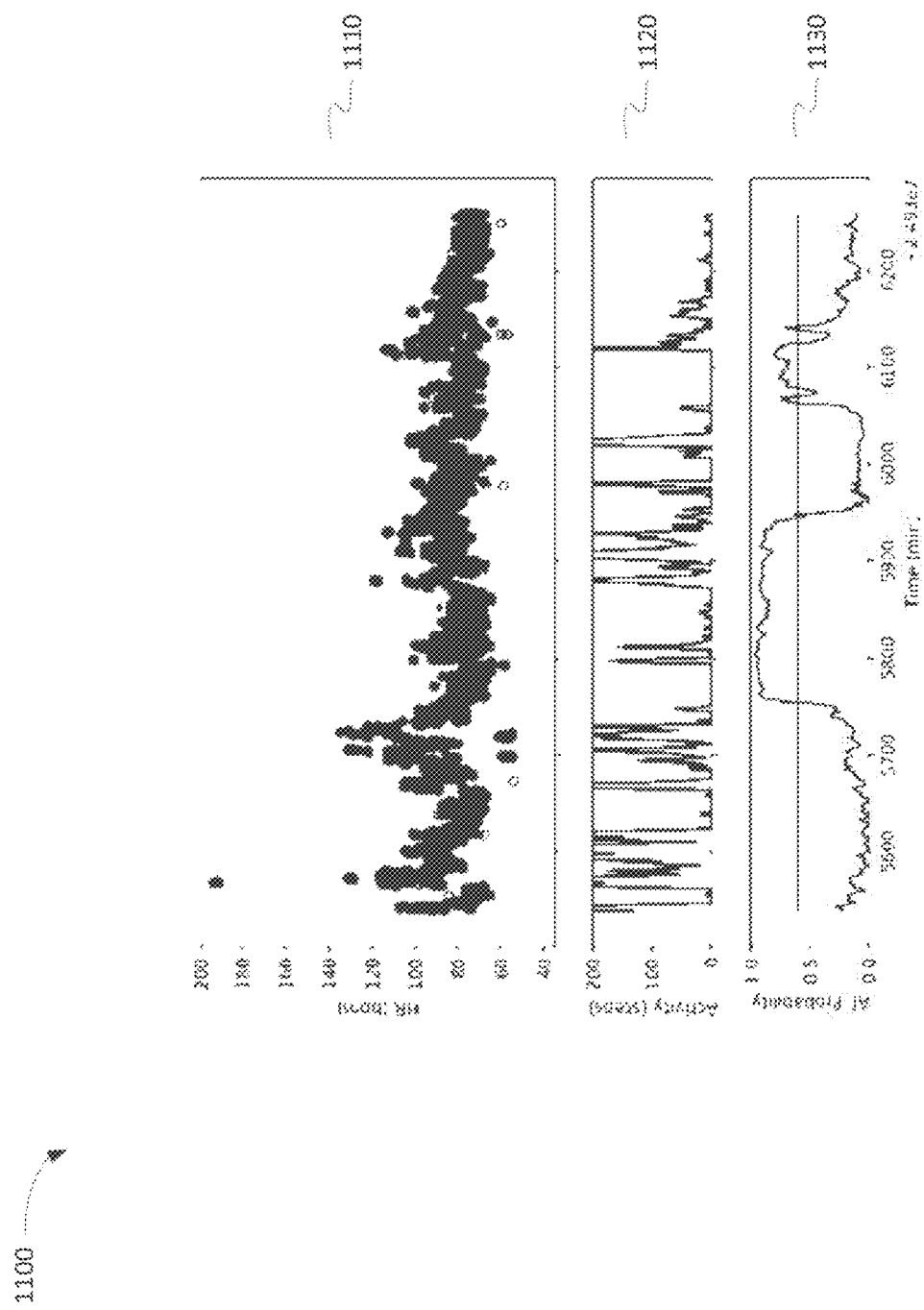
FIG. 11 depicts hypothetical data plots to demonstrate application of some embodiments as described herein.

FIG. 11 depicts example data 1100 analyzed based on low-fidelity data to generate a high-fidelity output prediction or detection, according to some embodiments as described herein. While described with reference to detection of atrial fibrillation, similar data may be generated for additional predictions of high-fidelity diagnosis based on low-fidelity measurements. The first chart 1110 shows heart rate calculations over time for a user. The heart rate may be determined based on PPG data or other heart rate sensors. The second chart 1120 shows activity data for a user during the same time period. For example, the activity data may be determined based on step count, or other measurements of movement of the user. The third chart 1130 shows a classifier output from a machine learning model and a horizontal threshold for when a notification is generated. A machine learning model may generate the prediction based on an input of low-fidelity measurements. For example, the data in the first chart 1110 and the second chart 1120 may be analyzed by a machine learning system as described further above. The result of the machine learning system analysis may be provided as the atrial fibrillation probability shown in chart 1130. When the probability is over a threshold value, shown in this case as above 0.6 confidence, a health monitoring system can trigger a notification or other alert for the user, a physician, or other users associated with the user.

In some embodiments, the data in charts 1110 and 1120 may be provided as continuous measurements to a machine learning system. For example, the heart rate and activity levels may be generated as measurements every 5 seconds in order an accurate measurement. A segment of time with multiple measurements can then be input to a machine learning model. For example, the previous hour of data can be used as an input to the machine learning model. In some embodiments, shorter or longer periods of time may be provided rather than one hour. As shown in FIG. 11, the output chart 1130 provides an indication of periods of time in which a user is undergoing an abnormal health event. For example, the periods when the prediction is over a certain confidence level may be used by a health monitoring system to determine atrial fibrillation. This value can then be used to determine an atrial fibrillation burden on the user during the measured time period.

In some embodiments, a machine learning model to generate the predicted output in chart 1130 may be trained based on labeled user data. For example, the labeled user data may be provided based on high-fidelity data (such as an ECG reading) taken at a time period when low-fidelity data (e.g., PPG, heart rate) and other data (e.g., activity level or steps) is also available. In some embodiments, the machine learning model is designed to determine if there was likely atrial fibrillation during a preceding time period. For example, the machine learning model may take an hour of low-fidelity data as an input and provide a likelihood there was an event. Accordingly, training data may include hours of recorded data for a population of individuals. The data can be health-event-labeled-times when a condition was diagnosed based on high-fidelity data. Accordingly, if there was a health-event labeled time based on high-fidelity data, the machine learning model may determine that any one-hour window of low-fidelity data with that event that is input into the untrained machine learning model should provide a prediction of the health-event. The untrained machine learning model can then be updated based on comparing the prediction with the label. After repeating for a number iterations and determining that the machine learning model has converged, it may be used by a health monitoring system to monitor for atrial fibrillation of users based on low-fidelity data. In various embodiments, other conditions than atrial fibrillation may be detected using low-fidelity data.

Figure 12:
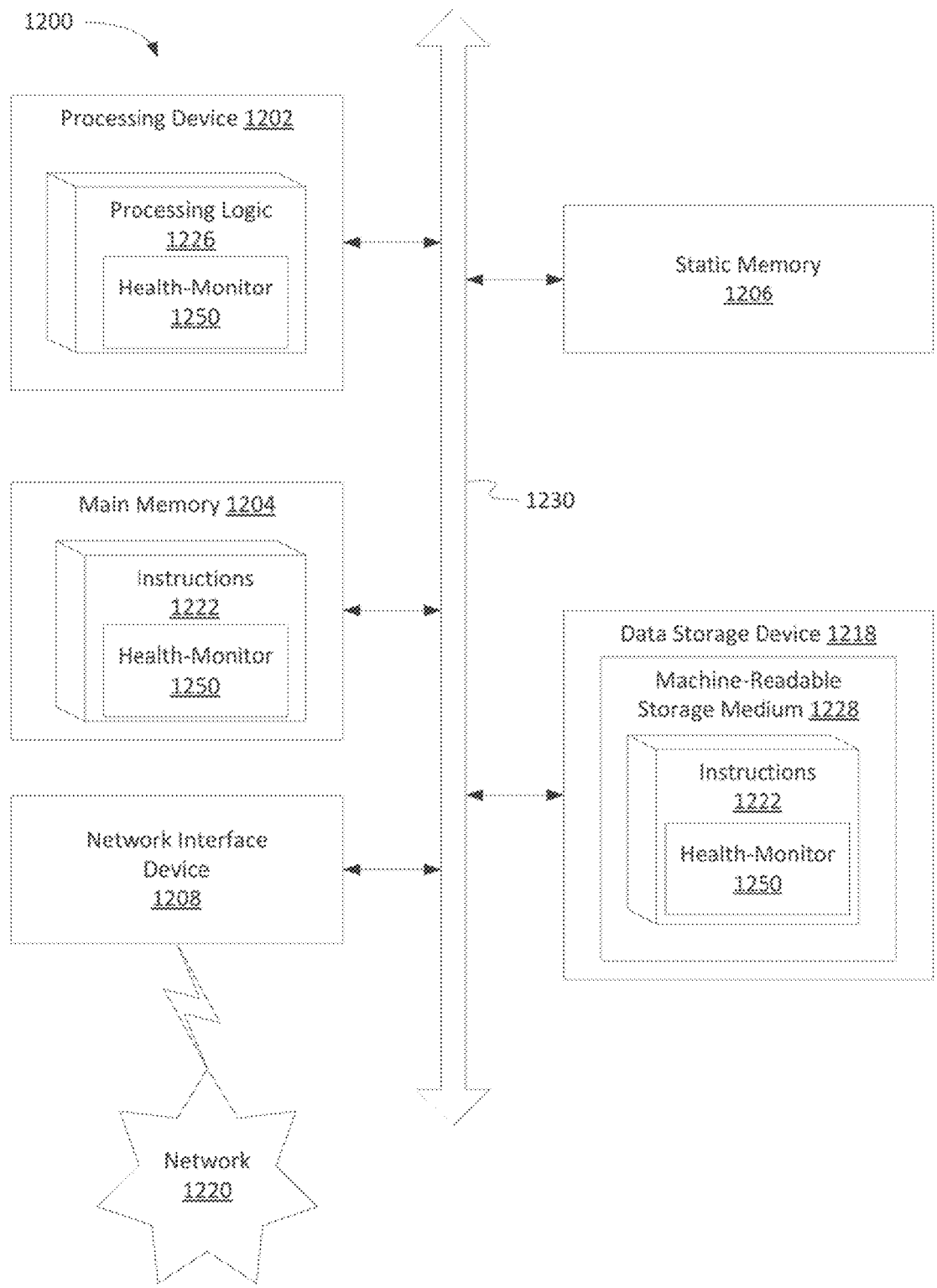
FIG. 12 depicts systems and devices in accordance with some embodiments as described herein.

FIG. 12 illustrates a diagrammatic representation of a machine in the example form of a computer system 1200 within which a set of instructions, for causing the machine to perform any one or more of the methodologies discussed herein, may be executed. In alternative embodiments, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, a switch or bridge, a hub, an access point, a network access control device, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. In one embodiment, computer system 1200 may be representative of a server, mobile computing device, wearable, or the like configured to perform health monitoring as described herein.

The exemplary computer system 1200 includes a processing device 1202, a main memory 1204 (e.g., read-only memory (ROM), flash memory, dynamic random access memory (DRAM)), a static memory 1206 (e.g., flash memory, static random access memory (SRAM), etc.), and a data storage device 1218, which communicate with each other via a bus 1230. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Processing device 1202 represents one or more general-purpose processing devices such as a microprocessor, central processing unit, or other processing device. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 1202 may also be one or more special-purpose processing devices such as an application specific integrated circuit (ASIC), a field programmable gate array (FPGA), a digital signal processor (DSP), network processor, or the like. The processing device 1202 is configured to execute processing logic 1226, which may be one example of a health-monitor 1250 and related systems for performing the operations and steps discussed herein.

The data storage device 1218 may include a machine-readable storage medium 1228, on which is stored one or more set of instructions 1222 (e.g., software) embodying any one or more of the methodologies of functions described herein, including instructions to cause the processing device 1202 to execute a health-monitor 1250 and related processes as described herein. The instructions 1222 may also reside, completely or at least partially, within the main memory 1204 or within the processing device 1202 during execution thereof by the computer system 1200; the main memory 1204 and the processing device 1202 also constituting machine-readable storage media. The instructions 1222 may further be transmitted or received over a network 1220 via the network interface device 1208.

The machine-readable storage medium 1228 may also be used to store instructions to perform a method for monitoring user health, as described herein. While the machine-readable storage medium 1228 is shown in an exemplary embodiment to be a single medium, the term "machine-readable storage medium" should be taken to include a single medium or multiple media (e.g., a centralized or distributed database, or associated caches and servers) that store the one or more sets of instructions. A machine-readable medium includes any mechanism for storing information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into may other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

In addition to the embodiments described above, the present disclosure includes, without limitation, the following example implementations.

Some example implementations provide a method of monitoring a user's cardiac health. The method can include, receiving measured health-indicator data and other-factor data of a user at a first time, inputting, by a processing device, the health-indicator data and other-factor data into a machine learning model, wherein the machine learning model generates predicted health-indicator data at the next time step, receiving the user's data at the next time step, determining, by the processing device, a loss at the next time step, wherein the loss is a measure between the predicted health-indicator data at the next time step and the user's measured health-indicator data at the next time step, determining that the loss exceeds a threshold, and outputting, in response to determining that the loss exceeds a threshold, a notification to the user.

In some example implementations of the method of any example implementations the trained machine learning model is a trained generative neural network. In some example implementations of the method of any example implementations the trained machine learning model is a feed-forward network. In some example implementations of the method of any example implementations the trained machine learning model is a RNN. In some example implementations of the method of any example implementations the trained machine learning model is a CNN.

In some example implementations of the method of any example implementations the trained machine learning model is trained on training examples from one or more of: a healthy population, a population with heart disease, and the user.

In some example implementations of the method of any example implementations the loss at the next time step is the absolute value of the difference between the predicted health-indicator data at the next time step and the user's measured health-indicator at the next time step.

In some example implementations of the method of any example implementations the predicted health-indicator data is a probability distribution, and wherein the predicted health-indicator data at the next time step is sampled from the probability distribution.

In some example implementations of the method of any example implementations the predicted health-indicator data at the next time step is sampled according to a sampling technique selected from the group consisting of: the predicted health-indicator data at maximum probability; and random sampling the predicted health-indicator data from the probability distribution.

In some example implementations of the method of any example implementations the predicted health-indicator data is a probability distribution ($\beta$), and wherein the loss is determined based on a negative logarithm of the probability distribution at the next time step evaluated with the user's measured health-indicator at the next time step. In some example implementations of the method of any example implementations the method further includes self-sampling of the probability distribution.

In some example implementations of the method of any example implementations the method further includes averaging the predicted health-indicator data over a period of time steps, averaging the user's measured health-indicator data over the period of time steps, and determining the loss based on an absolute value difference between the predicted health-indicator data and the measured health-indicator data.

In some example implementations of the method of any example implementations the measured health-indicator data comprises PPG data. In some example implementations of the method of any example implementations the measured health-indicator data comprises heart rate data.

In some example implementations of the method of any example implementations the method further includes resampling irregularly spaced heart rate data onto a regularly spaced grid, wherein the heart rate data is sampled from the regularly spaced grid.

In some example implementations of the method of any example implementations the measured health-indicator data is one or more health-indicator data selected from the group consisting of: PPG data, heart rate data, pulse oximeter data, ECG data, and blood pressure data.

Some example limitations provide an apparatus comprising a mobile computing device comprising a processing device, a display, a heath-indicator data sensor, and a memory having instructions stored thereon that, when executed by the processing device, cause the processing device to: receive measured health-indicator data from the health-indicator data sensor at time and other-factor data at a first time, input health-indicator data and other-factor data, into a trained machine learning model, and wherein the trained machine learning model generates predicted health-indicator data at a next time step, receive measured health-indicator data and other-factor data at the next time step, determine a loss at the next time step, wherein the loss is a measure between the predicted health-indicator data at the next time step and the measured health-indicator data at the next time step, and output a notification if the loss at the next time step exceeds a threshold.

In some example implementations of any example apparatus the trained machine learning model comprises a trained generative neural network. In some example implementations of any example apparatus the trained machine learning model comprises a feed-forward network. In some example implementations of any example apparatus the trained machine learning model is a RNN. In some example implementations of the method of any example implementations the trained machine learning model is a CNN.

In some example implementations of any example apparatus the trained machine learning model is trained on training examples from one of the group consisting of: a healthy population, a population with heart disease and the user.

In some example implementations of any example apparatus the predicted health-indicator data is a point prediction of the user's health-indicator the next time step, and wherein the loss is the absolute value of the difference between the predicted health-indicator data and the measured health-indicator data at the next time step.

In some example implementations of any example apparatus the predicted health-indicator data is sampled from a probability distribution generated from the machine learning model.

In some example implementations of any example apparatus the predicted health-indicator data is sampled according to a sampling technique selected from the group consisting of: a maximum probability; and random sampling from the probability distribution.

In some example implementations of any example apparatus the predicted health-indicator data is a probability distribution ($\beta$), and wherein the loss is determined based on a negative logarithm of $\beta$ evaluated with the user's measured health-indicator at the next time step.

In some example implementations of any example apparatus the processing device is further to define a function $\alpha$ ranging from 0 to 1, wherein $I_t$ comprises a linear combination the user's measured health-indicator data and the predicted health-indicator data as a function of $\alpha$.

In some example implementations of any example apparatus the processing device is further to perform self-sampling of the probability distribution.

In some example implementations of any example apparatus the processing device is further to: average, using an averaging method, the predicted health-indicator data sampled from the probability distribution over a period of time steps, average, using the averaging method, the user's measured health-indicator data over the period of time steps, defining the loss the absolute value of the averaged predicted health-indicator data and the measured health-indicator data.

In some example implementations of any example apparatus the averaging method comprises one or more methods selected from the group consisting of: calculating an average, calculating an arithmetic mean, calculating a median and calculating a mode.

In some example implementations of any example apparatus the measured health-indicator data comprises PPG data from a PPG signal. In some example implementations of any example apparatus the measured health-indicator data is heart rate data. In some example implementations of any example apparatus the heart rate data is collected by resampling irregularly spaced heart rate data onto a regularly spaced grid, and the heart rate data is sampled from the regularly spaced grid. In some example implementations of any example apparatus the measured health-indicator data is one or more health-indicator data selected from the group consisting of: PPG data, heart rate data, pulse oximeter data, ECG data, and blood pressure data.

In some example implementations of any example apparatus the mobile device is selected from the group consisting of: a smart watch; a fitness band; a computer tablet; and a laptop computer.

In some example implementations of any example apparatus the mobile device further comprises a user high-fidelity sensor, wherein the notification requests the user to obtain high-fidelity measurement data, and wherein the processing device is further to: receive an analysis of the high-fidelity measurement data; label the user measured health-indicator data with the analysis to generate labeled user health-indicator data; and use labeled user health-indicator data as a training example to train a trained personalized high-fidelity machine learning model.

In some example implementations of any example apparatus the trained machine learning model is stored on the memory. In some example implementations of any example apparatus the trained machine learning model is stored on a remote memory, wherein the remote memory is separate from the computing device and wherein the mobile computing device is a wearable computing device. In some example implementations of any example apparatus the trained personalized high-fidelity machine learning model is stored on the memory. In some example implementations of any example apparatus the trained personalized high-fidelity machine learning model is stored on a remote memory, wherein the remote memory is separate from the computing device and wherein the mobile computing device is a wearable computing device.

In some example implementations of any example apparatus the processing device is further to predict that the user is experiencing atrial fibrillation and determine an atrial fibrillation burden of the user.

Some example implementations provide a method of monitoring a user's cardiac health. The method can include receiving measured low fidelity user health-indicator data and other-factor data at a first time, inputting data comprising the user health-indicator data and other-factor data at the first time, into a personalized high-fidelity trained machine learning model, wherein the personalized high-fidelity trained machine learning model makes a prediction if the user's health-indicator data is abnormal, and if the prediction is abnormal, sending a notification that the user's health is abnormal.

In some example implementations of the method of any example implementations the trained personalized high-fidelity machine learning model is trained on measured low fidelity user health-indicator data labeled with an analysis of high-fidelity measurement data.

In some example implementations of the method of any example implementations the analysis of high-fidelity measurement data is based on user specific high-fidelity measurement data.

In some example implementations of the method of any example implementations the personalized high-fidelity machine learning model outputs a probability distribution, wherein the prediction is sampled from the probability distribution.

In some example implementations of the method of any example implementations the prediction is sampled according to a sampling technique selected from the group consisting of the prediction at a maximum probability and random sampling the prediction from the probability distribution.

In some example implementations of the method of any example implementations an averaged prediction is determined by averaging, using an averaging method, the prediction over a period of time steps, and wherein the averaged prediction is used to determine if the user's health-indicator data is normal or abnormal.

In some example implementations of the method of any example implementations the averaging method comprises one or more methods selected from the group consisting of: calculating an average, calculating an arithmetic mean, calculating a median and calculating a mode.

In some example implementations of the method of any example implementations the personalized high-fidelity trained machine learning model is stored in a memory of a user wearable device. In some example implementations of the method of any example implementations the measured health-indicator data and other-factor data are time segments of data over a time period.

In some example implementations of the method of any example implementations the personalized high-fidelity trained machine learning model is stored in a remote memory, wherein the remote memory is located remotely from a user wearable computing device.

In some example implementation a health monitoring apparatus may include a mobile computing device comprising a microprocessor, a display, a user heath-indicator data sensor, and a memory having instructions stored thereon that, when executed by the microprocessor, cause the processing device to: receive measured low fidelity health-indicator data and other-factor data at a first time, wherein measured health-indicator data is obtained by the user health-indicator data sensor, input data comprising the health-indicator data and other-factor data at the first time, into a trained high-fidelity machine learning model, wherein the trained high-fidelity machine learning model makes a prediction if the user's health-indicator data is normal or abnormal; and in response to the prediction being abnormal, send a notification to at least the user that the user's health is abnormal.

In some example implementations of health monitoring apparatus of any example implementation the trained high-fidelity machine learning model is a trained high-fidelity generative neural network. In some example implementations of health monitoring apparatus of any example implementation wherein the trained high-fidelity machine learning model is a trained recurrent neural network (RNN). In some example implementations of health monitoring apparatus of any example implementation the trained high-fidelity machine learning model is a trained feed-forward neural network. In some example implementations of health monitoring apparatus of any example implementation the trained high-fidelity machine learning model is a CNN.

In some example implementations of health monitoring apparatus of any example implementation the trained high-fidelity machine learning model is trained on measured user health-indicator data labeled with based on user specific high-fidelity measurement data.

In some example implementations of health monitoring apparatus of any example implementation the trained high-fidelity machine learning model is trained on low fidelity health-indicator data labeled based on high-fidelity measurement data, wherein the low fidelity health-indicator data and the high-fidelity measurement data is from a population of subjects.

In some example implementations of health monitoring apparatus of any example implementation the high-fidelity machine learning model outputs a probability distribution, wherein the prediction is sampled from the probability distribution.

In some example implementations of health monitoring apparatus of any example implementation the prediction is sampled according to a sampling technique selected from the group consisting of: the prediction at a maximum probability; and random sampling the prediction from the probability distribution.

In some example implementations of health monitoring apparatus of any example implementation an averaged prediction is determined by averaging, using an averaging method, the prediction over a period of time steps, and wherein the averaged prediction is used to determine if the user's health-indicator data is normal or abnormal.

In some example implementations of health monitoring apparatus of any example implementation the measured health-indicator data and other-factor data are time segments of data over a time period.

In some example implementations of health monitoring apparatus of any example implementation the averaging method comprises one or more methods selected from the group consisting of: calculating an average, calculating an arithmetic mean, calculating a median and calculating a mode.

In some example implementations of health monitoring apparatus of any example implementation the personalized high-fidelity trained machine learning model is stored in the memory. In some example implementations of health monitoring apparatus of any example implementation the personalized high-fidelity trained machine learning model is stored in a remote memory, wherein the remote memory is located remotely from the wearable computing device. In some example implementations of health monitoring apparatus of any example implementation the mobile device is selected from the group consisting of: a smart watch; a fitness band; a computer tablet; and a laptop computer.

What is claimed is:

1. An apparatus, comprising:
a processing device;
a heath-indicator data sensor operatively coupled to the processing device;
and a memory having instructions stored thereon that, when executed by the processing device, cause the processing device to:
receive measured low-fidelity health-indicator data and other-factor data of a user at a time, wherein the measured low-fidelity health-indicator data is obtained by the health-indicator data sensor;
input a set of data comprising the low-fidelity health-indicator data and the other-factor data into a trained high-fidelity machine learning model, wherein the trained high-fidelity machine learning model is configured to predict whether an event is normal or abnormal, wherein if the high-fidelity machine learning model predicts that the event will be abnormal, the high-fidelity machine learning model further calculates an amount of time the event will be abnormal; and in response to the event being abnormal, send a notification that a health of the user is abnormal.

2. The apparatus according to claim 1, wherein the trained high-fidelity machine learning model comprises one or more of a trained high-fidelity generative neural network, a trained recurrent neural network (RNN), a trained feed-forward neural network, or a trained feed-forward neural network.

3. The apparatus according to claim 1, wherein the trained high-fidelity machine learning model is trained on measured user health-indicator data labeled with user-specific high-fidelity measurement data.

4. The apparatus according to claim 1, wherein the trained high-fidelity machine learning model is trained on low-fidelity health-indicator data labeled with high-fidelity measurement data, wherein the low-fidelity health-indicator data and the high-fidelity measurement data is from a population of subjects.

5. The apparatus according to claim 1, wherein the high-fidelity machine learning model outputs a probability distribution, wherein the prediction is sampled from the probability distribution.

6. The apparatus according to claim 5, wherein the prediction is sampled according to a sampling technique selected from the group consisting of: the prediction at a maximum probability; and random sampling the prediction from the probability distribution.

7. The apparatus according to claim 5, wherein an averaged prediction is determined by averaging, using an averaging method, the prediction over a period of time steps, and wherein the averaged prediction is used to determine if the event is normal or abnormal.

8. The apparatus according to claim 1, wherein the apparatus is selected from the group consisting of: a smart watch; a fitness band; a computer tablet; and a laptop computer.

9. The apparatus according to claim 1, wherein each of the low-fidelity health-indicator data and other factor-data are time segments of data over a time period.

10. The apparatus according to claim 1, wherein the low-fidelity health-indicator data comprises a record of a heart rate of the user prior to the time, the other-factor data comprises a record of activity level, and the prediction comprises a prediction that the user experienced atrial fibrillation during the record of the heart rate of the user prior to the time.

11. The apparatus according to claim 1, wherein the processing device is further to:
receive a set of training data, wherein the training data comprises labeled low-fidelity health-indicator data from a population of individuals, corresponding other-factor data from the population individuals, wherein the labeled low-fidelity indicator data is labeled with corresponding high-fidelity data from the population of individuals;

input an interval of the labeled low-fidelity health-indicator data and the corresponding other-factor data into the trained high-fidelity machine learning model; and update the labeled high-fidelity machine learning model by comparing an output from the trained high-fidelity machine learning model to the labeled high-fidelity data.

12. A method, comprising:

receiving, by a processing device, measured low-fidelity health-indicator data and other-factor data of a user at a time, wherein the measured low-fidelity health-indicator data is obtained by a user health-indicator data sensor;

inputting, by the processing device, data comprising the low-fidelity health-indicator data and other-factor data at the time into a trained high-fidelity machine learning model, wherein the trained high-fidelity machine learning model is configured to predict whether an event is normal or abnormal, wherein if the high-fidelity machine learning model predicts that the event will be abnormal, the high-fidelity machine learning model further calculates an amount of time the event will be abnormal; and in response to the event being abnormal, sending a notification that a health of the user is abnormal.

13. The method according to claim 12, wherein the trained high-fidelity machine learning model comprises one or more of a trained high-fidelity generative neural network, a trained recurrent neural network (RNN), a trained feed-forward neural network, or a trained feed-forward neural network.

14. The method according to claim 12, wherein each of the low-fidelity health-indicator data and the other factor-data are time segments of data over a time period.

15. The method according to claim 12, wherein the low-fidelity health-indicator data comprises a record of a heart rate of the user prior to the time, the other-factor data comprises a record of activity level, the prediction comprises a prediction that the user experienced atrial fibrillation during the record of the heart rate of the user prior to the time, and the notification comprises and an indication to take an ECG.

16. The method according to claim 12, wherein the trained high-fidelity machine learning model is trained on low-fidelity health-indicator data labeled with high-fidelity measurement data, wherein the low-fidelity health-indicator data and the high-fidelity measurement data is from a population of subjects.

17. The method according to claim 12, wherein the high-fidelity machine learning model outputs a probability distribution, wherein the prediction is sampled from the probability distribution.

18. The method according to claim 17, wherein the prediction is sampled according to a sampling technique selected from the group consisting of: the prediction at a maximum probability; and random sampling the prediction from the probability distribution.

19. The method according to claim 17, wherein an averaged prediction is determined by averaging, using an averaging method, the prediction over a period of time steps, and wherein the averaged prediction is used to determine if the event is normal or abnormal.

20. The method according to claim 12, further comprising:

receiving a set of training data, wherein the training data comprises labeled low-fidelity health-indicator data from a population of individuals, corresponding other-factor data from the population individuals, wherein the labeled low-fidelity indicator data is labeled with corresponding high-fidelity data from the population of individuals;

inputting an interval of the labeled low-fidelity health-indicator data and the corresponding other-factor data into the trained high-fidelity machine learning model; and updating the labeled high-fidelity machine learning model by comparing an output from the trained high-fidelity machine learning model to the labeled high-fidelity data.

* * * * *